United States Patent
Croan et al.

(10) Patent No.: US 10,319,475 B1
(45) Date of Patent: Jun. 11, 2019

(54) METHOD AND APPARATUS FOR DETERMINING RELATIONSHIPS BETWEEN MEDICATIONS AND SYMPTOMS

(71) Applicant: Enigami Systems, Inc., Denver, CO (US)

(72) Inventors: Clifton D. Croan, Denver, CO (US); William F. Graf, Golden, CO (US)

(73) Assignee: ENIGAMI SYSTEMS, INC., Denver, CO (US)

(*) Notice: Subject to any disclaimer, the term of this patent is extended or adjusted under 35 U.S.C. 154(b) by 613 days.

(21) Appl. No.: 14/739,723

(22) Filed: Jun. 15, 2015

Related U.S. Application Data

(60) Provisional application No. 62/012,133, filed on Jun. 13, 2014.

(51) Int. Cl.
*G16H 50/20* (2018.01)
*G06F 19/00* (2018.01)
*G06Q 10/10* (2012.01)
*G06Q 50/26* (2012.01)

(52) U.S. Cl.
CPC ......... *G16H 50/20* (2018.01); *G06F 19/3456* (2013.01); *G06Q 10/10* (2013.01); *G06Q 50/26* (2013.01)

(58) Field of Classification Search
CPC ... G06F 19/327; G06F 19/3456; G06Q 10/00; A61B 5/0002; G16H 10/20; G16H 50/70
See application file for complete search history.

(56) References Cited

U.S. PATENT DOCUMENTS

| | | | |
|---|---|---|---|
| 4,279,824 A | 7/1981 | McKinney |
| 5,252,490 A | 10/1993 | ElSohly |
| 6,113,940 A | 9/2000 | Brooke |
| 6,328,992 B1 | 12/2001 | Brooke |
| 7,379,885 B1 | 5/2008 | Zakim |
| 8,337,908 B2 | 12/2012 | Letzel |
| 8,445,034 B1 | 5/2013 | Coles |
| 8,518,653 B2 | 8/2013 | Takkinen |
| 8,753,696 B1 | 6/2014 | Lewis |
| 8,884,100 B2 | 11/2014 | Page |
| 8,895,078 B2 | 11/2014 | Mueller |
| 8,906,429 B1 | 12/2014 | Kolsky |

(Continued)

OTHER PUBLICATIONS

Emerging Clinical Applications for Cannabis and Cannabinoids—A Review of the Recent Scientific Literature; Armentano; NORML; Nov. 20, 2017 (Year: 2017).*

(Continued)

*Primary Examiner* — John A Pauls
(74) *Attorney, Agent, or Firm* — Vobach IP Law, LLC

(57) ABSTRACT

In accordance with one embodiment, a method can be implemented that includes enlisting via a computer network a plurality of participants to report one or more effects of their respective usage of a substance; confirming that a prospective participant is located in a state where use of the substance is legal; receiving from each of the one or more participants via the computer network one or more self-assessment reports of any physical, emotional, or mental responses or any combination thereof to the substance; and processing the one or more self-assessment reports with a computer processor to determine if the substance has an effect on a particular symptom or condition.

24 Claims, 26 Drawing Sheets

(56) References Cited

U.S. PATENT DOCUMENTS

| | | |
|---|---|---|
| 8,910,630 B2 | 12/2014 | Todd |
| 8,980,941 B2 | 3/2015 | Hospodor |
| 9,050,631 B2 | 6/2015 | Raichart |
| 9,066,910 B2 | 6/2015 | Rosenblatt |
| 9,095,554 B2 | 8/2015 | Lewis |
| 9,095,563 B2 | 8/2015 | Sekura |
| 9,149,499 B1 | 10/2015 | Robinson |
| 9,199,960 B2 | 12/2015 | Ferri |
| 9,220,294 B2 | 12/2015 | McCullough |
| 9,259,449 B2 | 2/2016 | Raderman |
| 9,333,229 B2 | 5/2016 | Bjorncrantz |
| 9,351,953 B2 | 5/2016 | Stodola |
| 9,370,164 B2 | 6/2016 | Lewis |
| 9,408,986 B2 | 8/2016 | McCullough |
| 9,480,647 B2 | 11/2016 | Benson |
| 9,504,723 B2 | 11/2016 | Kolsky |
| 9,538,733 B2 | 1/2017 | Jones |
| 9,546,960 B2 | 1/2017 | Pierce |
| 9,565,865 B2 | 2/2017 | Bhairam |
| 9,629,886 B2 | 4/2017 | Franklin |
| 9,632,069 B2 | 4/2017 | Jackson |
| 9,642,317 B2 | 5/2017 | Lewis |
| 9,694,040 B2 | 7/2017 | Scialdone |
| 9,730,911 B2 | 8/2017 | Verzura |
| 9,765,308 B2 | 9/2017 | Page |
| 9,808,494 B2 | 11/2017 | Barringer |
| 9,852,393 B2 | 12/2017 | Walden |
| 9,867,859 B2 | 1/2018 | Raderman |
| 9,913,868 B1 | 3/2018 | Alfiere |
| 9,974,821 B2 | 5/2018 | Kennedy |
| 9,988,763 B2 | 6/2018 | Ramaratnam |
| 10,021,838 B1 | 7/2018 | Gustafik |
| 10,105,343 B2 | 10/2018 | Kubby |
| 2002/0188471 A1* | 12/2002 | Schaefer ............ G06F 19/3456 705/2 |
| 2004/0210457 A1* | 10/2004 | Sameh ................ G06Q 10/10 705/2 |
| 2006/0241972 A1* | 10/2006 | Lang .................... G06F 19/327 705/2 |
| 2007/0033066 A1 | 2/2007 | Ammer et al. |
| 2007/0106626 A1* | 5/2007 | Mundie ............... G06N 99/005 706/20 |
| 2007/0226012 A1 | 9/2007 | Salgado et al. |
| 2007/0280431 A1 | 12/2007 | Alpsten et al. |
| 2008/0021341 A1* | 1/2008 | Harris ................. A61B 5/0031 600/544 |
| 2008/0052318 A1 | 2/2008 | Iliff |
| 2008/0177149 A1 | 7/2008 | Weinert et al. |
| 2009/0055220 A1 | 2/2009 | Rapaport et al. |
| 2009/0112624 A1 | 4/2009 | Brown |
| 2009/0125333 A1* | 5/2009 | Heywood ............ A61B 5/0002 705/3 |
| 2009/0292554 A1* | 11/2009 | Schultz ................ G06Q 10/06 705/2 |
| 2010/0274495 A1* | 10/2010 | Sobol .................... G16H 10/20 702/19 |
| 2012/0158420 A1* | 6/2012 | Lacal ................... G06Q 10/00 705/2 |

OTHER PUBLICATIONS

Researching the Potential Medical Benefits and Risks of Marijuana; Throckmorton; FDA; Jul. 13, 2016 (Year: 2016).*

Choosing the Correct Statistical Test [online], Mar. 10, 2015 [retrieved by Archive.org on Mar. 10, 2015 from URL http://bama.ua.edu/~jleeper/627/choosestat.html][also available at https://web.archive.org/web/20150310144023/http://bama.ua.edu/~jleeper/627/choosestat.html].

Choosing the Correct Statistical Test [online], Aug. 26, 2015 [retrieved by Archive.org on Aug. 26, 2015 from URL http://bama.ua.edu/~jleeper/627/choosestat.html][also available at https://web.archive.org/web/20150826083004/http://bama.ua.edu:80/~jleeper/627/choosestat.html ].

Ex parte Galloway, appeal No. 2017-004696, (PTAB May 24, 2018).

Ex parte Bhogal, appeal No. 2016-008742, (PTAB Mar. 19, 2018).

Ex parte Young, appeal No. 2017-006731, (PTAB Jun. 29, 2018).

* cited by examiner

MY MMJ LOG
powered by Enigami Medical Cannabis, LLC

ADD CONDITION

I have a diagnosed condition of

Severe Nausea

Notice: if your Condition is not in the list, let us know so we can add it!
Notice: PTSD has been added to all states for a Veterans Study. This does not mean that it is a Qualifying Condition for all the states!

I would like to monitor the following symptoms

Nausea

CANCEL                    DONE

© 2014, Enigami Medical Cannabis, LLC|ALL RIGHTS RESERVED | Patent Pending         Terms of Service | Privacy Policy

FIG. 6

MY MMJ LOG
powered by Enigami Medical Cannabis, LLC

ADD CONDITION

I have a diagnosed condition of
Choose a Condition....

- Cachexia
- Cancer
- Chronic Pain
- Epilepsy/Seizures
- Glaucoma
- HIV/AIDS
- Multiple Sclerosis/Muscle Spasticity
- Severe Nausea
- Chronic Nervous System Disorders
- Post Traumatic Stress Disorder , let us know so we can add it!
tes for a Veterans Study. This does not mean that it
s!

DONE

NEXT

| | Register | Enigami Symptom Tracker | |
|---|---|---|---|
| Hypervigilance ⟩ | exaggerated startle response ⟩ | feeling of detachment or estrangement from others ⟩ |
| markedly diminished interest/ participation in significant activities ⟩ | inability to recall an important aspect of the trauma ⟩ | efforts to avoid activities/places/ people that arouse recollection of the trauma ⟩ |
| efforts to avoid thoughts/ feelings/conversations associated with trauma ⟩ | recurrent distressing dreams of the event ⟩ | recurrent/intrusive distressing recollections of event (images/ thoughts/perceptions) ⟩ |
| physiological reactivity on exposure to int/external cues that symbolize/ resemble an aspect of event ⟩ | intense psych distress at exposure to int/external cues that symbolize/ resemble an aspect of event ⟩ | Acting/feel event recurring, reliving, illusion, hallucination, dissoc flashback – awake/intoxicated ⟩ |
| Persistent and exaggerated negative beliefs or expectations about oneself, others, or the world ⟩ | Persistent, distorted cognition about the cause or consequences of the traumatic event ⟩ | Persistent negative emotional state. ⟩ |
| Persistent inability to experience positive emotions ⟩ | Reckless or self-destructive behavior ⟩ | |

CANCEL          DONE

MY MMJ LOG
powered by Enigami Medical Cannabis, LLC

ADD MEDICATION

MEDICATION TYPE

Prescription
Over the Counter
Medical Cannabis

CANCEL    DONE

No Medications have been added yet. Click the button above to add a medication.

Back    NEXT

© 2014, Enigami Medical Cannabis, LLC|ALL RIGHTS RESERVED | Patent Pending    Terms of Service | Privacy Policy

FIG. 14

MY MMJ LOG
powered by Enigami Medical Cannabis, LLC

ADD MEDICATION

MEDICATION TYPE

[ Over the Counter ▸ ]

MEDICATION          AMOUNT

[ Choose a Medication ▸ ]   [ ex: 50 ▸ ] mg

FREQUENCY

[ Select a Frequency... ▸ ]

I take this medication for the following conditions:

[ Chronic Pain ˅ ]   [ Severe Nausea ˅ ]   [ Post Traumatic Stress Disorder ˅ ]

[ CANCEL ]                                           [ DONE ]

© 2014, Enigami Medical Cannabis, LLC|ALL RIGHTS RESERVED | Patent Pending          Terms of Service | Privacy Policy

FIG. 15

MY MMJ LOG
powered by Enigami Medical Cannabis, LLC

ADD MEDICATION

MEDICATION TYPE
[Over the Counter ▼]

MEDICATION          AMOUNT          FREQUENCY
[Melatonin ▼]       [3 ▼] mg        [1X Daily ▼]

I take this medication for the following conditions:

[Chronic Pain ⌄]   [Severe Nausea ⌄]   [Post Traumatic Stress Disorder ⌄]

[CANCEL]                                [DONE]

© 2014, Enigami Medical Cannabis, LLC | ALL RIGHTS RESERVED | Patent Pending    Terms of Service | Privacy Policy

FIG. 22 mymmjlog.com/#/register-Register | Enigami Symptom Tracker

Patient Dashboard | Enigami Symptom Tracker

Medical Cannabis, White Widow, 25mg, 3X Daily
(THC:15 CBD:1 CBC:1)

Over the Counter Melatonin, 3mg, 1X Daily

My Nausea for my Severe Nausea is at a severity level of:
☺ 1 2 3 4 ⑤ 6 7 8 9 ☹

My Difficulty falling or staying asleep for my Post Traumatic Stress Disorder is at a severity level of:
☺ 1 2 3 4 5 6 ⑦ 8 9 ☹

My feeling of detachment or estrangement from others for my Post Traumatic Stress Disorder is at a severity level of:
☺ 1 2 3 4 ⑤ 6 7 8 9 ☹

STEP 3: ADD NOTES (OPTIONAL)
Please list any changes to your regular routine, diet or workout activity.

Enter Notes Here....

LOG IT

© 2014,Enigami Medical Cannabis, LLC|ALL RIGHTS RESERVED | Patent Pending        Terms of Service | Privacy Policy

METHOD AND APPARATUS FOR DETERMINING RELATIONSHIPS BETWEEN MEDICATIONS AND SYMPTOMS

CROSS-REFERENCE TO RELATED APPLICATIONS

This application claims the benefit under 35 U.S.C. § 119(e) of U.S. provisional patent application 62/012,133, filed on Jun. 13, 2014 and titled "Method and Apparatus for Determining Relationships between Medications and Symptoms" which is hereby incorporated by reference in its entirety and for all purposes.

SUMMARY

In accordance with one embodiment, a method can be implemented that includes enlisting via a computer network a plurality of participants to report one or more effects of their respective usage of a substance; confirming that a prospective participant is located in a state where use of the substance is legal; receiving from each of the one or more participants via the computer network one or more self-assessment reports of any physical, emotional, or mental responses or any combination thereof to the substance; and processing the one or more self-assessment reports with a computer processor to determine if the substance has an effect on a particular symptom or condition.

In accordance with another embodiment, a method can be implemented that includes enlisting via a computer network a plurality of participants to report one or more effects of their respective cannabinoid usage; confirming that a prospective participant is located in a state where use of cannabinoids is legal; receiving from each of the one or more participants via the computer network one or more self-assessment reports of any physical, emotional, or mental responses or any combination thereof to at least one cannabinoid product wherein the at least one cannabinoid product is associated with a particular cannabinoid profile; and processing the one or more self-assessment reports with a computer processor to determine a cannabinoid or combination of cannabinoids having an effect on a particular symptom or condition.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. Other features, details, utilities, and aspects of the claimed subject matter will be apparent from the following more particular written Detailed Description of various implementations and implementations as further illustrated in the accompanying drawings and defined in the appended claims.

BRIEF DESCRIPTION OF THE DRAWINGS

Figure 1:
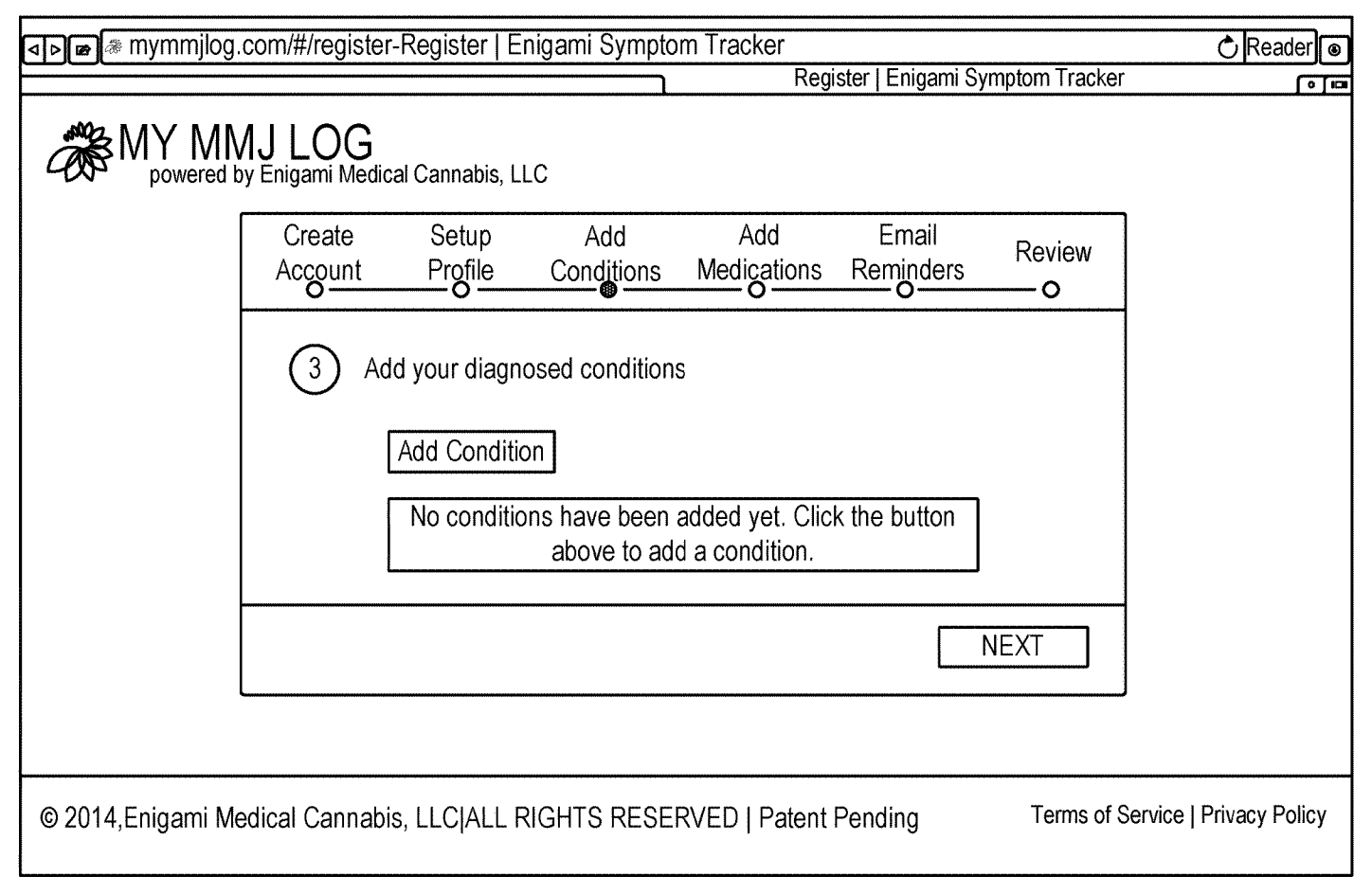

FIG. 1 illustrates an example of a user interface in which a user is prompted to enter a condition, in accordance with one embodiment.

FIG. 2 illustrates an example of a user interface in which a drop down menu allows a user to select a condition, in accordance with one embodiment.

FIG. 3 illustrates an example of a user interface in which the user has selected a diagnosed condition that the user desires to monitor, in accordance with one embodiment.

FIG. 4 illustrates an example of a user interface in which symptoms associated with a particular condition are listed for selection by a user, if the user should want to monitor those symptoms, in accordance with one embodiment.

FIG. 5 illustrates an example of a user interface from which a user can select a condition that the user wants to monitor, in accordance with one embodiment.

FIG. 6 illustrates an example of a user interface in which a user has selected a condition that the user wants to monitor, in accordance with one embodiment.

FIG. 7 illustrates an example of a user interface from which a user can select a condition that the user wants to monitor, in accordance with one embodiment.

FIG. 8 illustrates an example of a user interface in which symptoms associated with a particular condition are listed for selection by a user, if the user should want to monitor those symptoms, in accordance with one embodiment.

FIG. 9 illustrates a continuation of FIG. 8 as an example of a user interface in which symptoms associated with a particular condition are listed for selection by a user, if the user should want to monitor those symptoms, in accordance with one embodiment.

FIG. 10 illustrates an example of a user interface in which a user has selected available symptoms to monitor, in accordance with one embodiment.

FIG. 11 illustrates an example of a user interface that allows a user to add, edit, or remove a symptom or condition, in accordance with one embodiment.

FIG. 12 illustrates an example of a user interface in which a user can remove a condition and all of the selected associated symptoms, in accordance with one embodiment.

FIG. 13 illustrates an example of a user interface in which a user can add a particular medication or other substance that the user is taking, in accordance with one embodiment.

FIG. 14 illustrates an example of a user interface that allows a user to identify a medication by type, e.g., prescription, over the counter, or medical cannabis, in accordance with one embodiment.

FIG. 15 illustrates an example of a user interface that allows a user to specify the amount of medication (or other substance) that is being taken, frequency of administration, and conditions for which the medication is being taken, in accordance with one embodiment.

FIG. 16 illustrates an example of another user interface that allows a user to specify the amount of medication (or other substance) that is being taken, frequency of administration, and conditions for which the medication is being taken, in accordance with one embodiment.

FIG. 17 illustrates an example of a user interface that allows a user to specify a cannabinoid profile for a product that a user is taking, in accordance with one embodiment.

FIG. 18 illustrates an example of a user interface that allows a user to specify a second cannabinoid profile for a product that a user is taking, in accordance with one embodiment.

FIG. 19 illustrates an example of a user interface that allows a user to specify yet another cannabinoid profile for a product that a user is taking, in accordance with one embodiment.

FIG. 20 illustrates an example of a user interface that displays a summary of medications that the user has entered and an option to add still another medication, in accordance with one embodiment.

Figure 21:
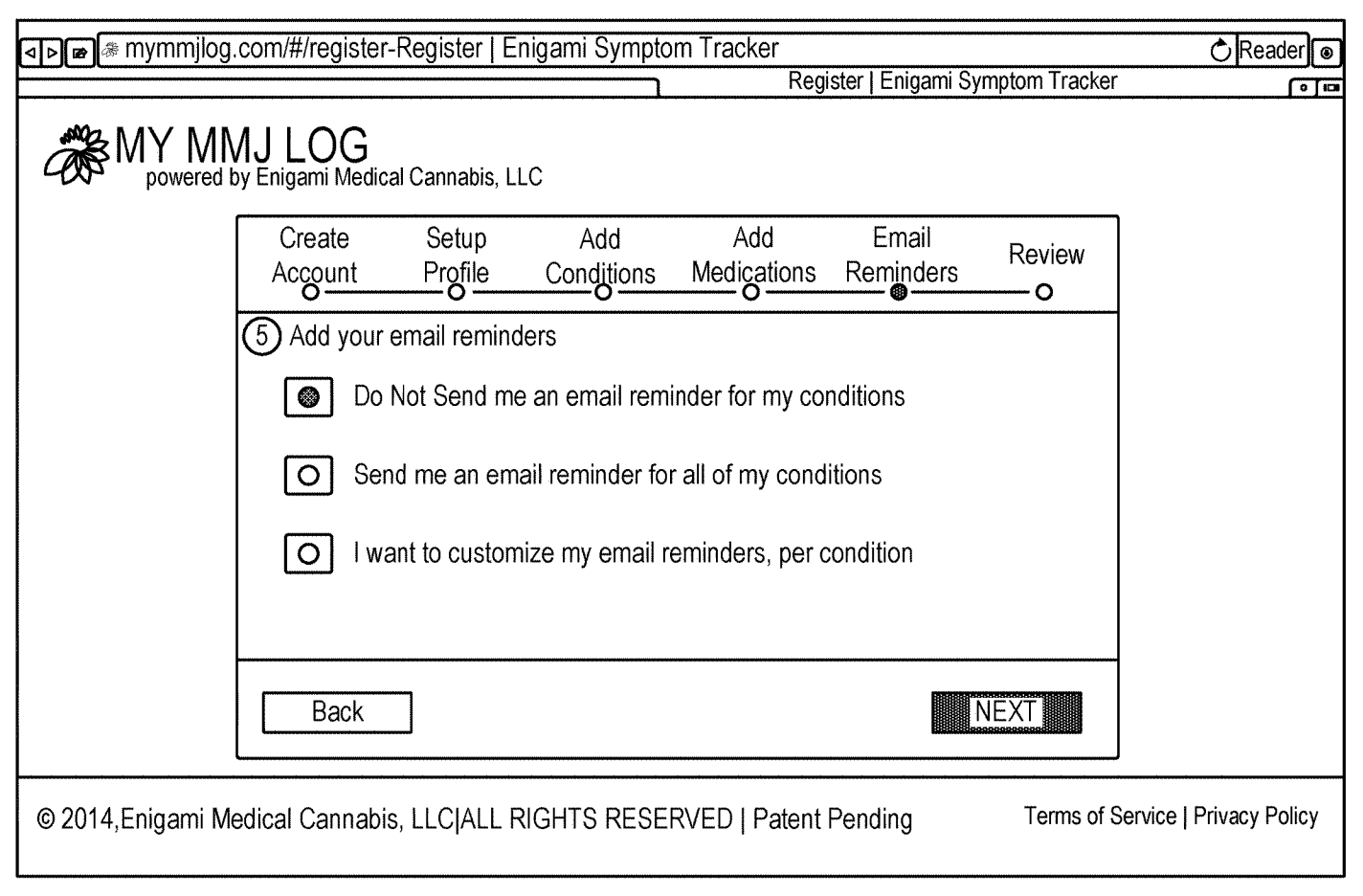

FIG. 21 illustrates an example of a user interface that allows a user to specify when an email or other electronic notification should be sent to the user about a selected condition, in accordance with one embodiment.

FIG. 22 illustrates an example of a user interface that allows a user to rate the severity of each symptom being monitored for that particular time and/or date, in accordance with one embodiment.

FIG. 23 is a continuation of the user interface shown in FIG. 22.

FIG. 25 illustrates a continuation of the user interface shown in FIG. 24 which allows a user to see comments made by the user during a selected time frame, in accordance with one embodiment.

DETAILED DESCRIPTION

Figure 24:
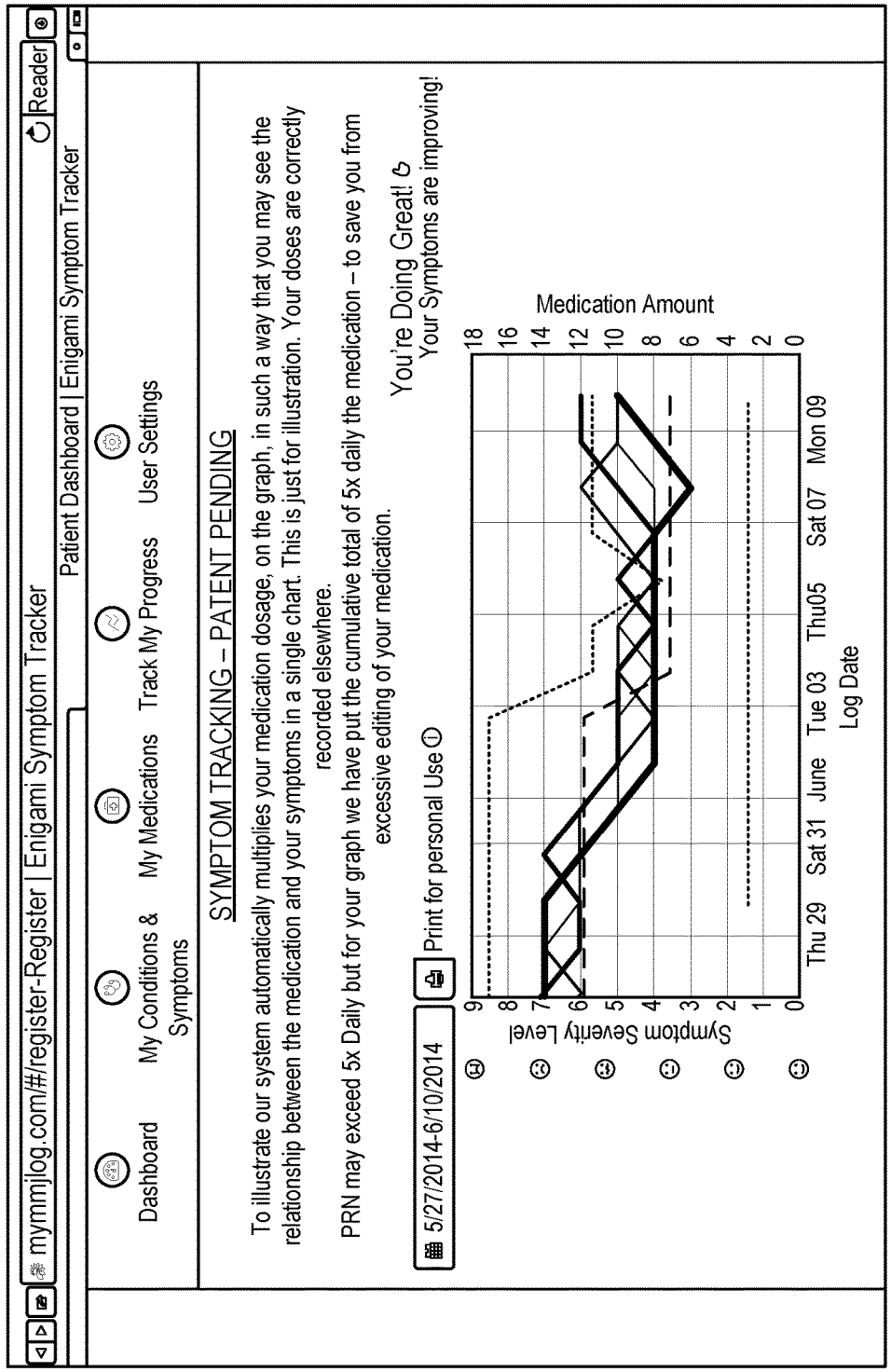
FIG. 24 illustrates an example of a user interface that displays selected symptom severity levels versus time/date as well as selected medication dosages versus time/date, in accordance with one embodiment.

Medical studies are often unreliable due to the limited number of participants that take part in conducting the studies. Because no two humans are the same, each individual reacts somewhat differently to the same substance being studied. If not enough subjects take part in a particular study, the results of the study can be unreliable or outright wrong or at least suffer from an unreliable statistical sample size. Historically, however, medical studies for new drugs have been conducted with limited test subject sample sizes.

One of the reasons that test subject sample sizes have been limited is due to the fact that studies are often funded by grants. Such grants often do not provide sufficient funds to perform a study of a large number of participants. Also, during studies, health professionals monitor participants for reactions to a new drug being tested. This typically requires significant funds to pay for the health professionals' services. Moreover, because some drugs can have unknown harmful effects, studies are sometimes designed to limit the number of participants to the least amount of participants that are required to produce a statistically relevant sample of participants.

While it is not uncommon for studies to be conducted to determine the effects of a new pharmaceutical, other types of substances are not so readily studied. For example, herbal substances or substances that were previously illegal are not often studied. Herbal remedies are widely used by the consuming public today. However, reliable information about their healing properties is difficult to come by. This is due to the fact that herbal substances are rarely the subjects of detailed studies. Moreover, some studies that have been done have been funded by the suppliers of the herbal substances themselves. Thus, it is not uncommon for someone considering use of an herbal substance to be skeptical about reports of a particular substance's purported healing properties. As a result, the reported benefits of many herbal substances are mainly anecdotal reports with no reliable study data to confirm the reported benefits.

Another difficulty in conducting studies is locating a sufficient number of test subjects who can contribute data. When a new herbal substance, for example, is first made available, it often has a limited number of users. Thus, there may be people in diverse locations throughout the country or world who are using the new herbal substance. The people using it could thus be described as homogeneous in their use of a substance but widely dispersed as to where they are physically located. As a result it is difficult to provide the test subjects with a test product or to follow up with the test subjects in person about their test results from using the test product.

Another example of a substance that lacks sufficient background studies is marijuana, sometimes referred to as cannabis. Extremely limited studies and no large scale clinical observational trials of marijuana have been conducted because marijuana has historically been an illegal substance in the vast majority of jurisdictions. Because of this, sufficient study has not been conducted to determine the effects, e.g., physical, emotional, or mental effects or a combination of those effects. Moreover, because there is a societal stigma attached to marijuana use, people are not readily willing to participate in formalized studies. As a result, little is known about the effects of marijuana usage.

Another difficulty in testing herbal products and previously illegal products is that the source and potency of a particular substance can vary across different suppliers. For example, a first supplier of an herbal medicine such as Echinacea might source its product from a first region of the world, whereas a second supplier might source its product from an entirely different region of the world. Moreover, the first supplier and second supplier might use different concentrations of the active ingredient in their respective Echinacea products. As a result, when participants from dispersed regions of a country or the world report their usage, the results can vary dramatically due to the different sources and different potencies of different products that are from the same general product category, e.g., all labeled as "Echinacea." This is true, as well, for a product like marijuana. Different strains of marijuana plants can contain different combinations of cannabinoids as well as different potencies of cannabinoids. Moreover, a strain of marijuana itself may vary in cannabinoid content over time. Thus, a user of a product sold under the name of "White Widow" in one part of the country might be using an entirely different marijuana product than a user who purchases "White Widow" in another part of the country. Furthermore, As a result, it is difficult without reliable testing and labeling to obtain reliable data for some types of generic products, such as herbal substances and recently legal substances from a physically disparate sample of test subjects.

In accordance with one embodiment, a new system is provided that allows for a sampling of a large number of participants. In addition, rather than requiring participants to appear before health professionals on a regular basis, the individual participants can record their medication and symptoms on a regular basis. This symptom and medication tracking can be performed remotely, e.g., by using a specially programmed computing device to record a participant's intake of medication and the participant's symptoms that are being monitored.

An example of this system can be illustrated with reference to testing cannabis products. Cannabis has not been studied very extensively due to the fact that the use of cannabis is illegal in many states. The use of cannabis is not illegal, however, under the state laws of an increasing number of states where cannabis has been approved for medical and/or recreational use.

Cannabis is a complicated substance. Cannabis contains multiple different substances that are referred to as cannabinoids. It is believed that there are at least eighty-four different cannabinoids. Cannabinoids are a class of diverse chemical compounds that act on cannabinoid receptors on cells that repress neurotransmitter release in the brain. Some examples of cannabinoids are CBD, CBN, THCA, CBDA, CBGA, CBG, CBC, CBL, CBV, THC, THCV, CBDV, CBCV, CBGV, and CBGM. Moreover, different types of cannabis plants produce different concentrations of these cannabinoids. The effect of each of these cannabinoids (as well as different combinations of cannabinoids and different dosages of cannabinoids) on the human body is not well known, if at all, because cannabinoids have not been extensively studied. Similarly, the effect on the human body of the use of different types of cannabis plants is also not well known, if at all.

Cannabis can be administered by a variety of methods. For example, it can be (a) inhaled, (b) taken orally in a fluid, (c) taken orally in a food, (d) vaporized, or (e) smoked. The effect on the human body caused by the mode of administration of a cannabinoid on the human body is not well known, if at all.

It is not uncommon for cannabis to be taken with other drugs or substances. The interaction of cannabinoids with other drugs or substances is not well known, if at all.

Referring now to FIGS. 1 through 26, an example of a system that can be used on a specially programmed computer is shown. This system may be utilized to test the effect of the use of a drug or substance, such as a cannabis product. An embodiment incorporating the user interfaces of FIGS. 1 through 26 is accessible at www.enigamisystems.com as the "Enigami Symptom Tracker" which is hereby incorporated by reference in its entirety and for all purposes.

The system of FIGS. 1 through 26 allows a user to set up an account and a profile before adding condition(s)/symptom(s) and medication information. It should be understood that in the following example, the user has already created an account and profile before entering his/her condition(s)/symptom(s) and medication information.

Figure 2:
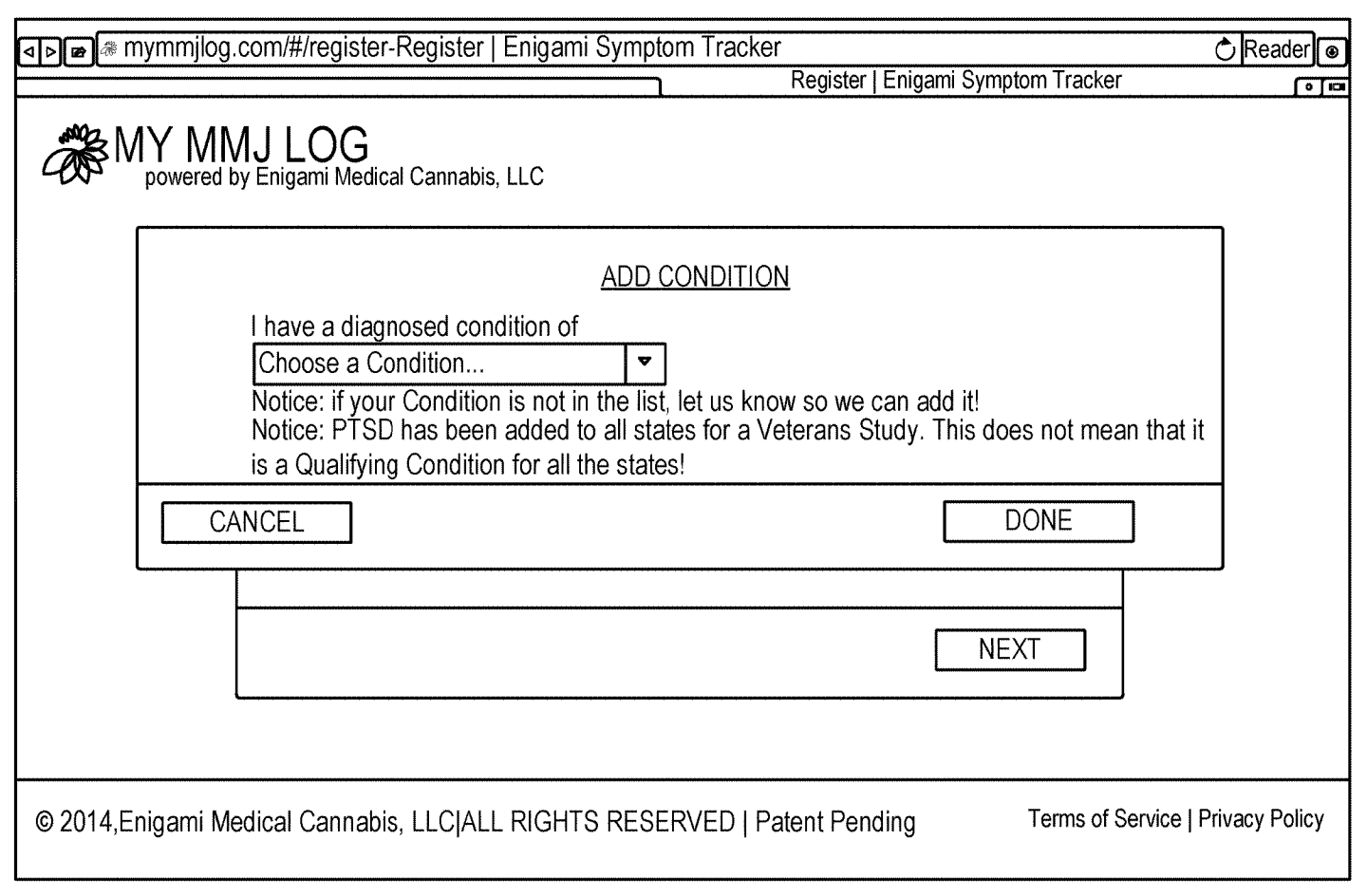
Figure 3:
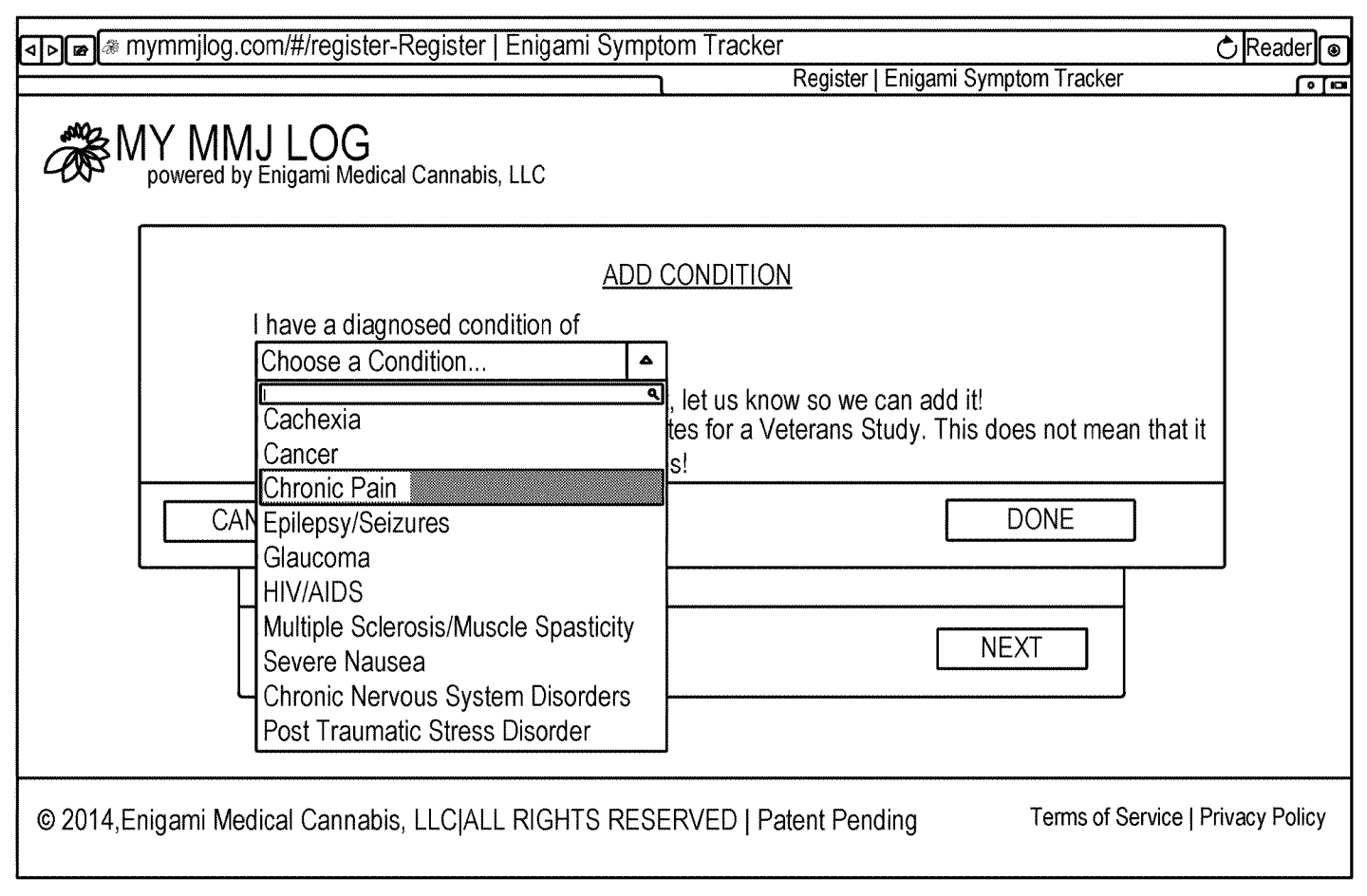

In FIG. 1, a user is prompted to enter a condition. The user can enter multiple conditions. Each condition is associated with predetermined symptoms that the user will later be able to monitor and to supply symptom data. FIG. 2 shows a second user interface with a drop down menu that allows the user to select a condition. For example, FIG. 3 shows a drop down menu. In FIG. 3, the user has selected "Chronic Pain" as a diagnosed condition that the user desires to monitor.

Figure 4:
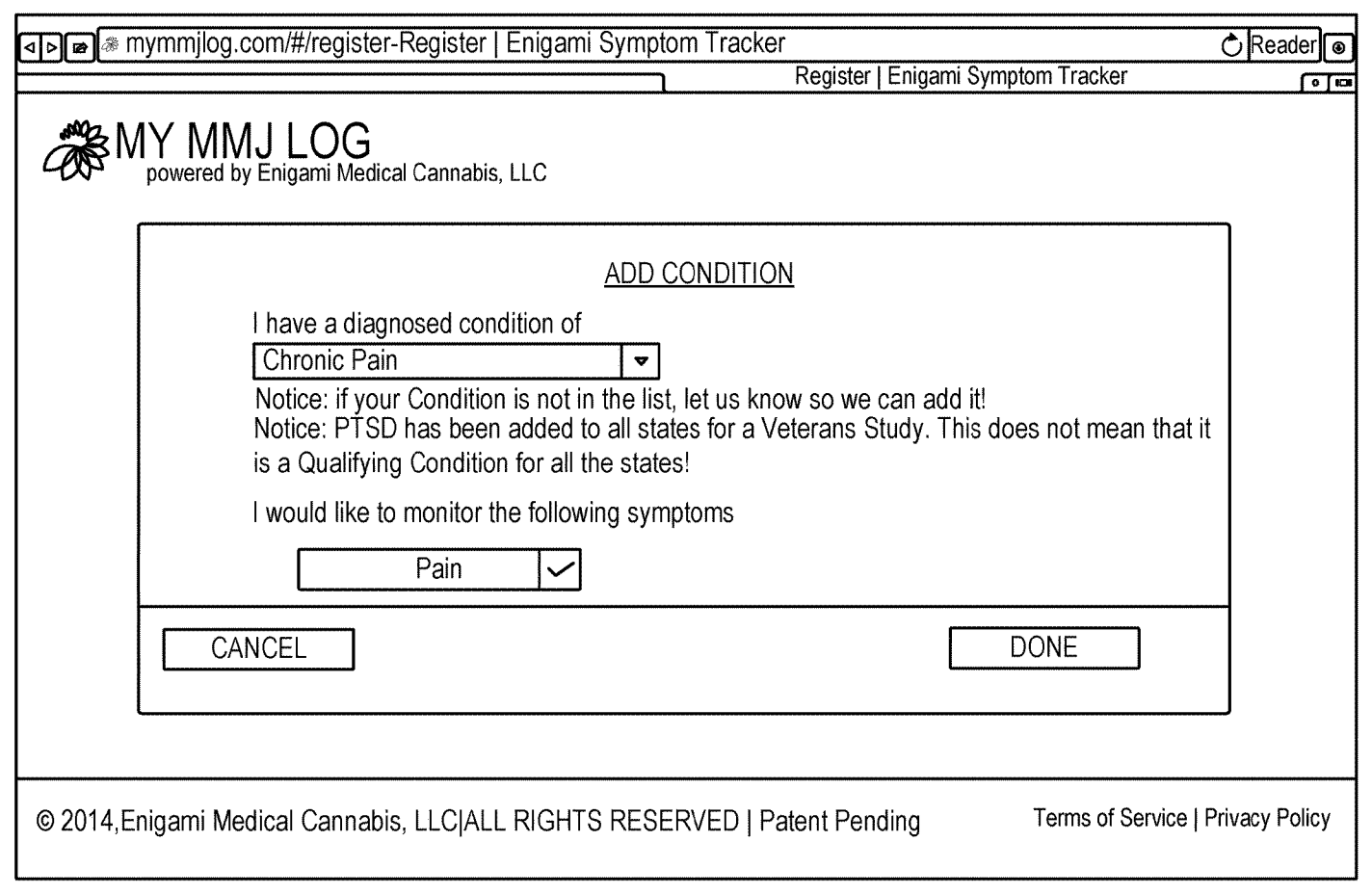

After selecting the desired condition, FIG. 4 shows that the condition has been added to the list of conditions being monitored by the user. At the bottom of FIG. 4, one can see the list of symptoms associated with the condition of "Chronic Pain." Namely, one symptom is available for monitoring and is labeled "Pain" in FIG. 4. A diagnosed condition is defined by one or more symptoms.

Figure 5:
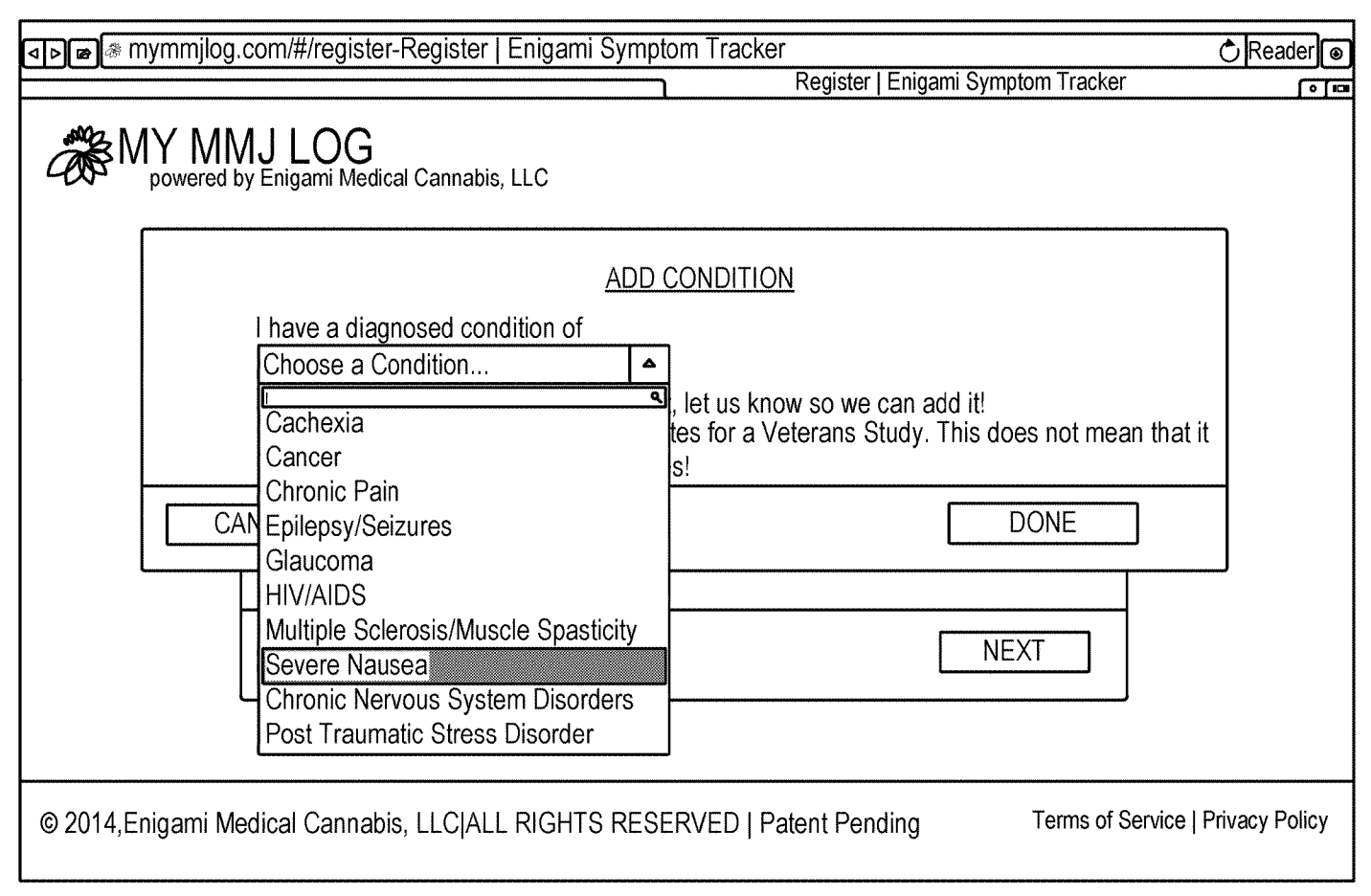

In FIG. 5, a new condition can be selected. In this example, the user has selected "Severe Nausea." As can be seen in FIG. 6, only one symptom is programmed for monitoring for the condition of "Severe Nausea" and that is the symptom of "Nausea."

Figure 8:
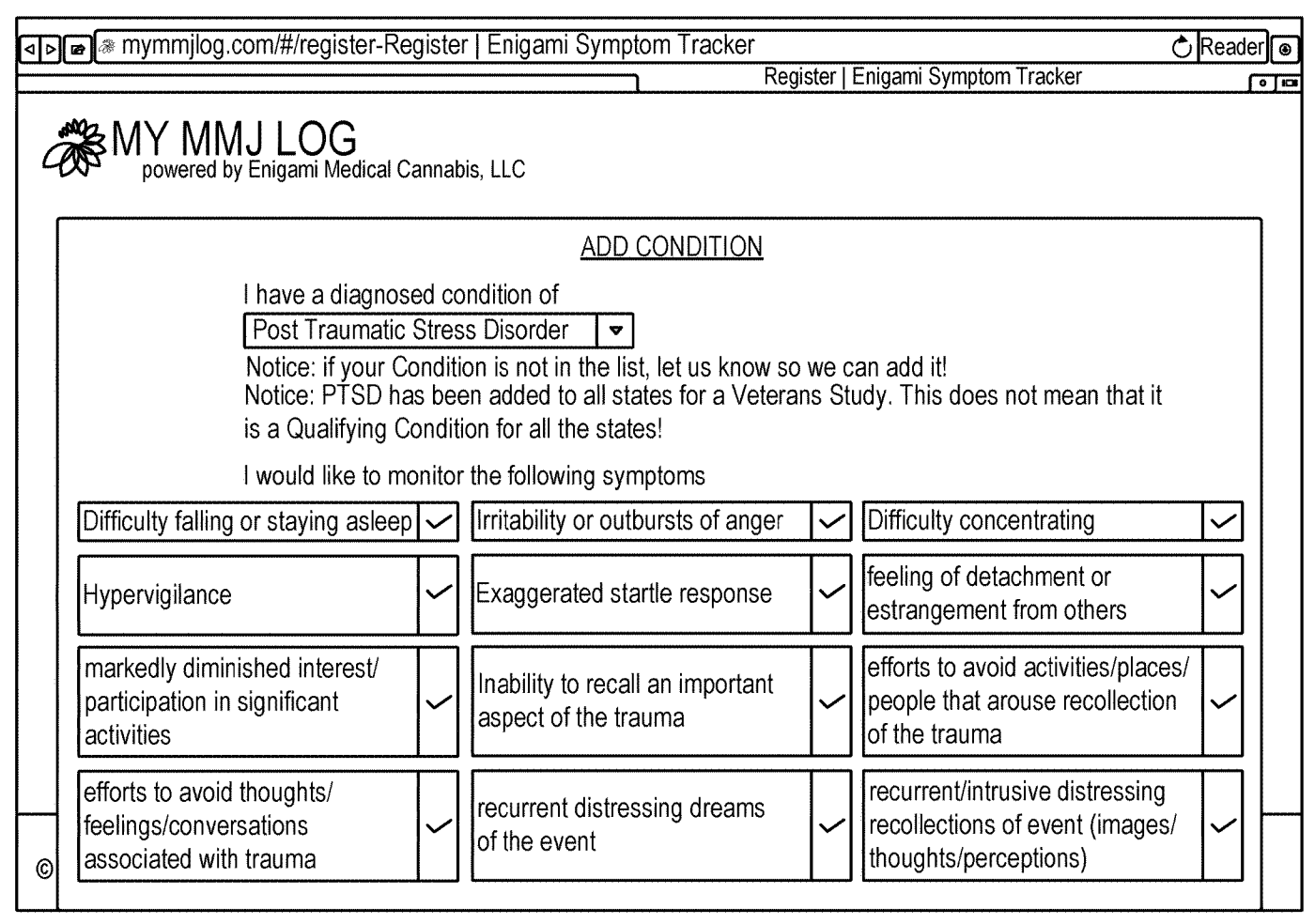

In FIG. 7, yet another condition can be selected for monitoring. In FIG. 7, the condition of "Post Traumatic Stress Disorder" is selected as a condition. FIGS. 8 and 9 illustrate that many different symptoms can be associated with the condition of diagnosed "Post Traumatic Stress Disorder." Different users may experience different symptoms more strongly than others. The system allows the user to select the symptoms that are most important to that particular user to monitor.

Figure 10:
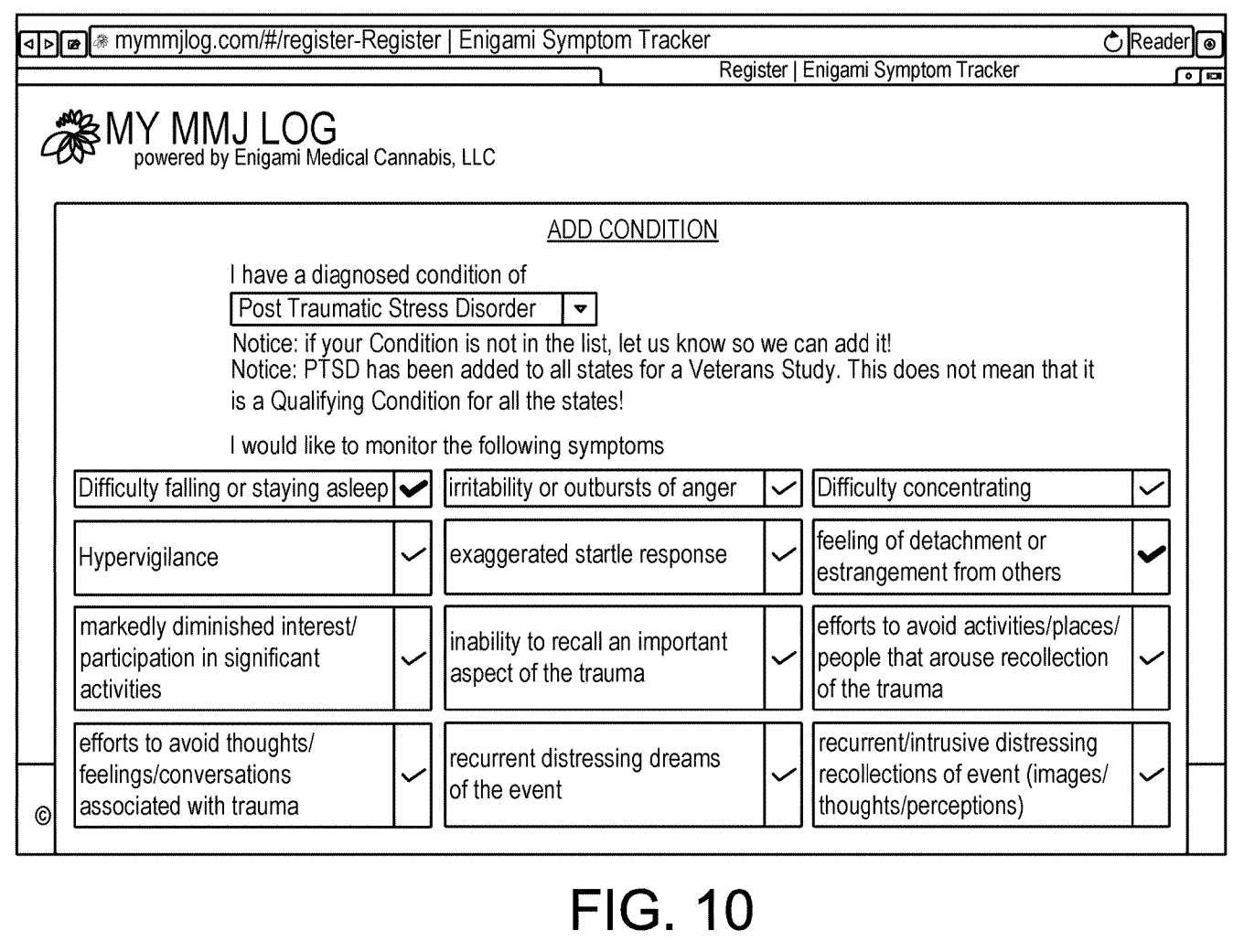

FIG. 10 shows that a user has selected the symptoms of "Difficulty falling or staying asleep" and "Feeling of detachment or estrangement from others."

Figure 11:
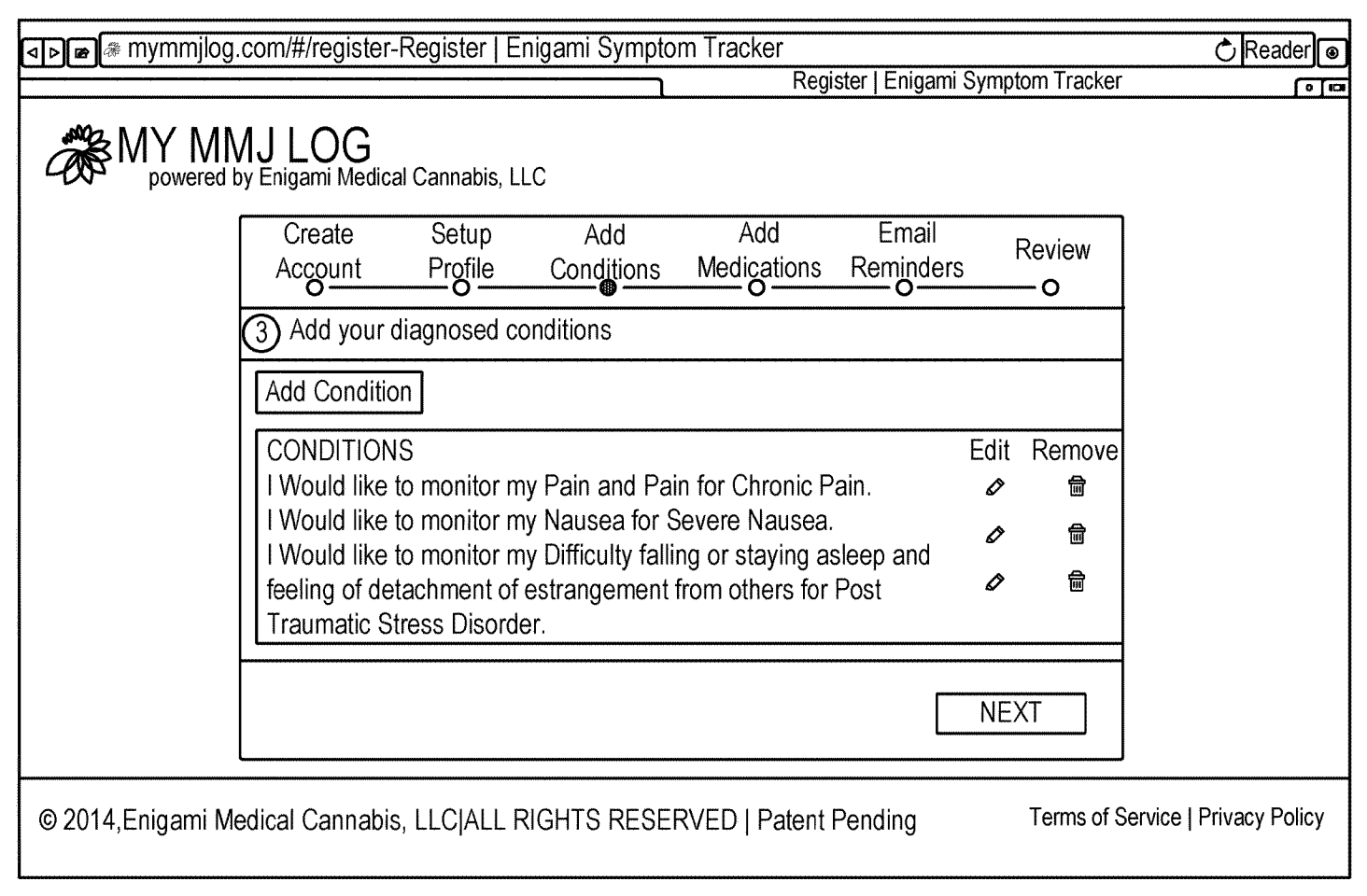
Figure 12:
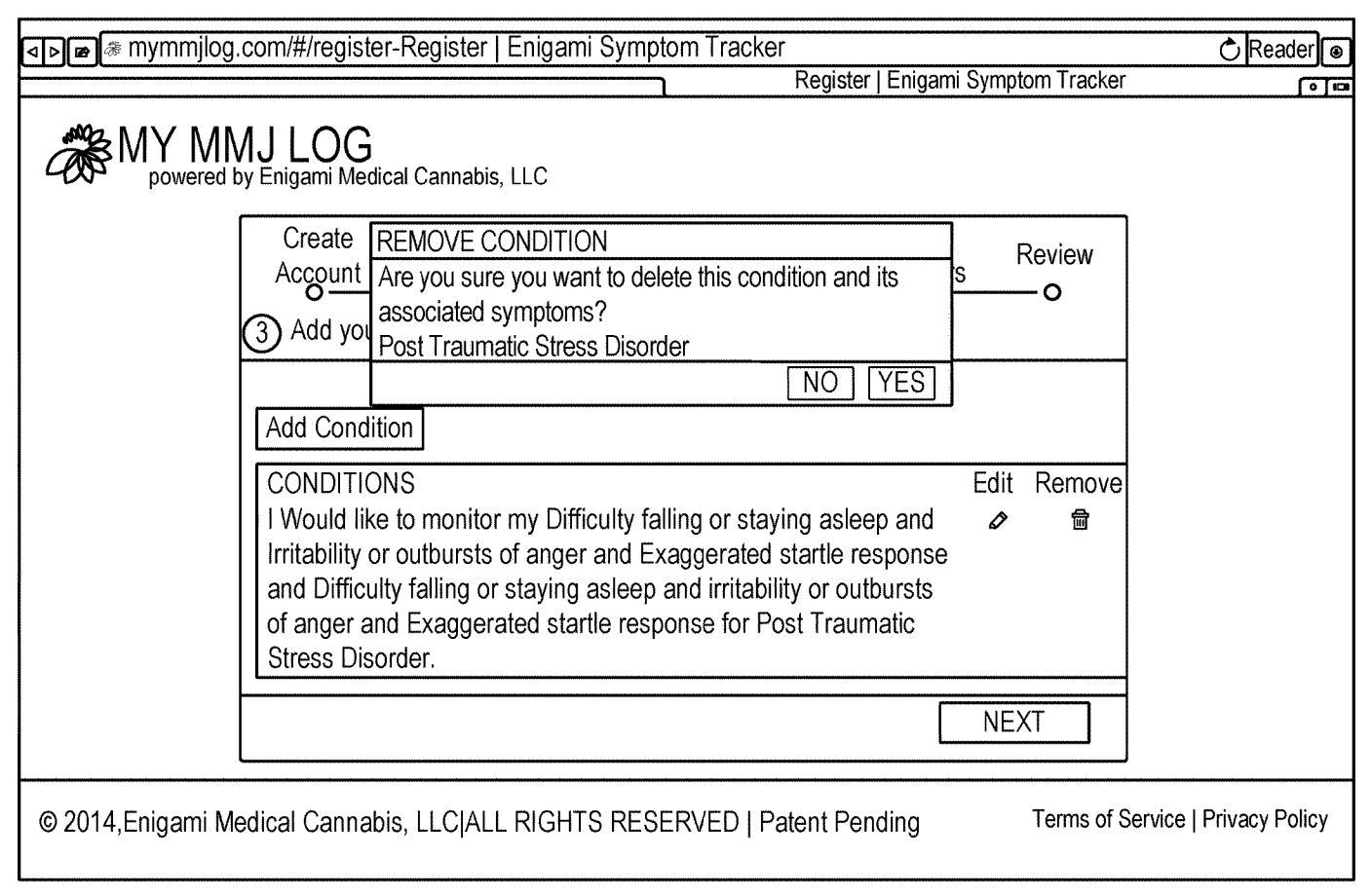

FIG. 11 illustrates the user interface screen that is displayed to a user once the user has finished selecting the conditions of "Chronic Pain," "Severe Nausea," and "Post Traumatic Stress Disorder." FIG. 11 also shows the symptoms that are being monitored for each condition. A user may use the edit or remove icons to edit or remove each condition from monitoring, as desired. For example, FIG. 12 illustrates a user interface screen that is displayed when the "Remove" icon is selected.

Figure 13:
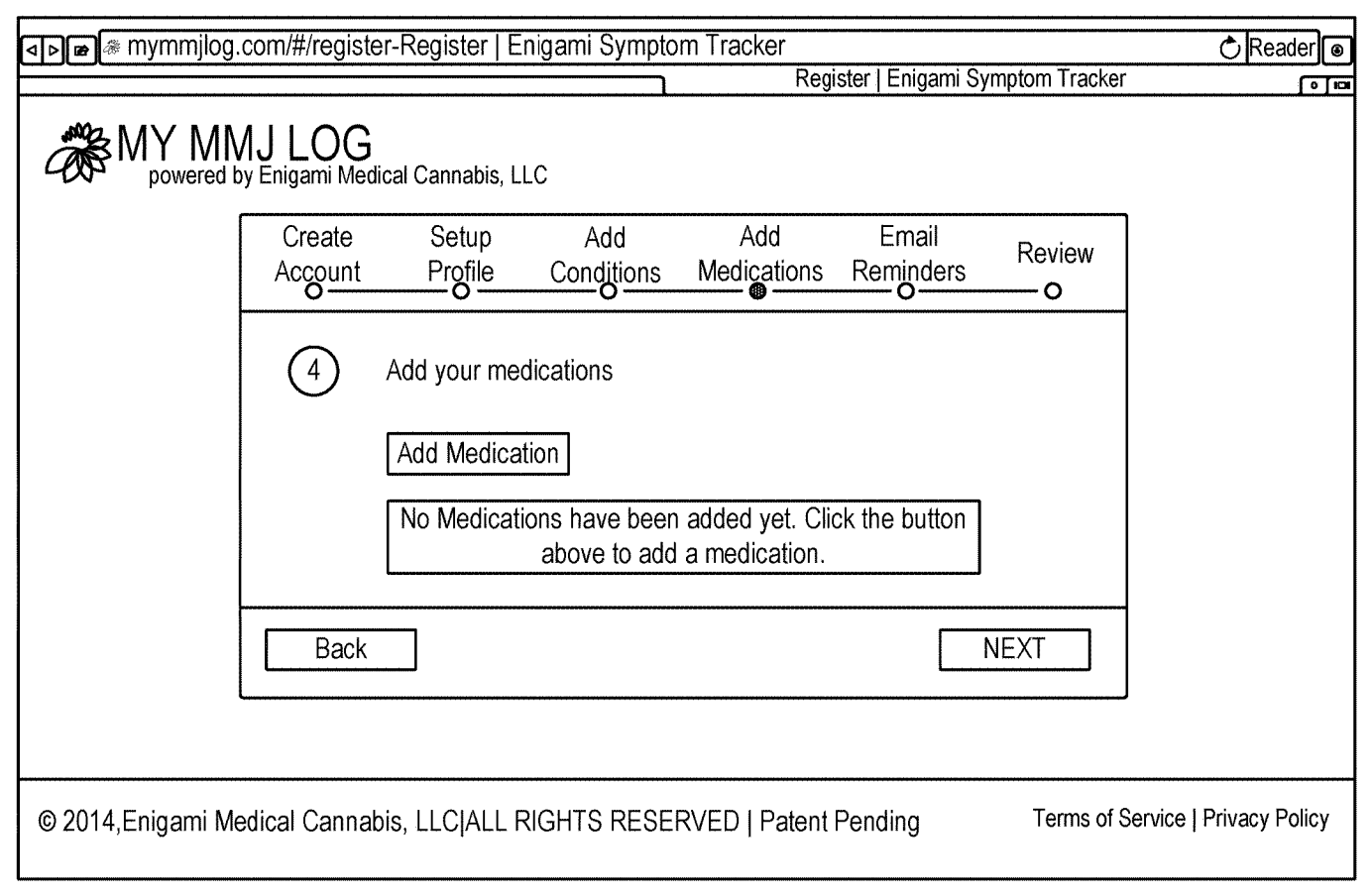

A user may also add medications by selecting the "Add Medications" icon. FIG. 13 illustrates a user interface screen for initiating the addition of medications. As shown in FIG. 14, a user can first be queried by medication type as to whether the medication to be added for monitoring is a prescription medication, an over-the-counter medication, or medical cannabis medication. For purposes of this patent, an over-the-counter medication can include herbal products and homeopathic products. In other embodiments, one might choose to monitor additional medication types, as well. For example, substances that are proposed products, or products being researched for pharmaceutical use could be monitored. Including all medications or substances that a user is taking can be useful for determining the interactive effect of different medicines or substances.

FIG. 15 illustrates a user interface screen that allows a user to choose or specify a medication by name (e.g., Ibuprofen), enter a dosage (e.g., 50 milligrams), select a frequency (e.g., taken 3 times a day). Moreover, FIG. 15 allows the user to specify what condition(s)/symptom(s) the medication is being taken for.

FIG. 16 illustrates an example where a user has entered information for the substance known as "Melatonin." The user has selected "Over the Counter" for medication type, "3 mg" for medication amount, "1× Daily" for frequency, and "Post Traumatic Stress Disorder" for the condition. This process can be repeated for each medication that is to be monitored.

Figure 17:
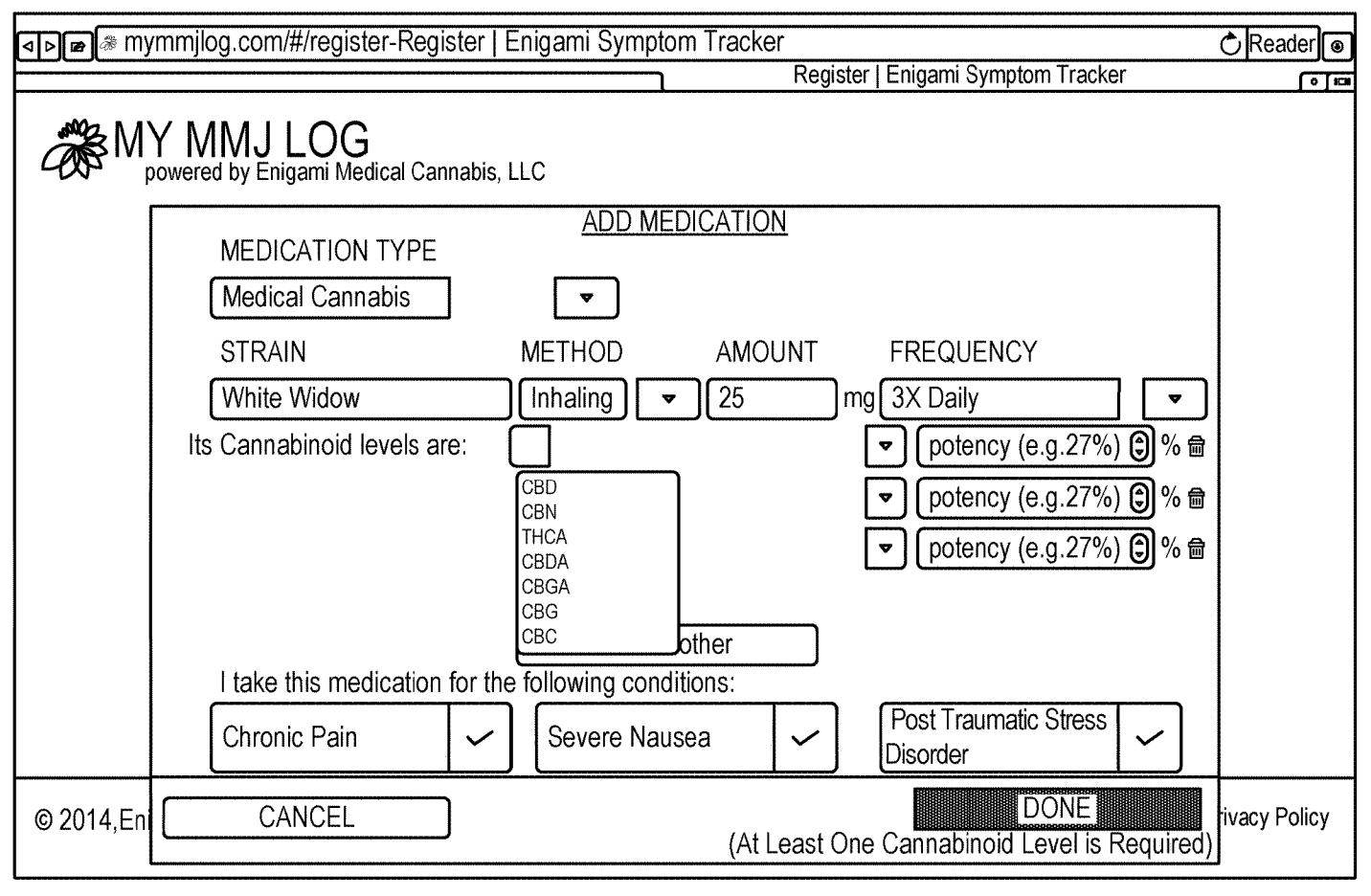

FIG. 17 illustrates an example of entering Cannabis as a medication. In FIG. 17, a user enters or specifies a particular strain that identifies the type of Cannabis being monitored. In one embodiment, a "strain" could be replaced by "product" so as to refer to a foodstuff, such as an edible product or a drink. In the cannabis industry, for example, edible and drinkable cannabis products are used. The strain can identify a particular type of cannabis, a particular type of cannabis product (e.g., a food type, drink type, a smoked type, or a vaporized type of cannabis product). FIG. 17 also shows that a user can select how the cannabis product will be administered. In FIG. 17, a user also selects an amount and frequency for the dosage of cannabis being administered.

Figure 18:
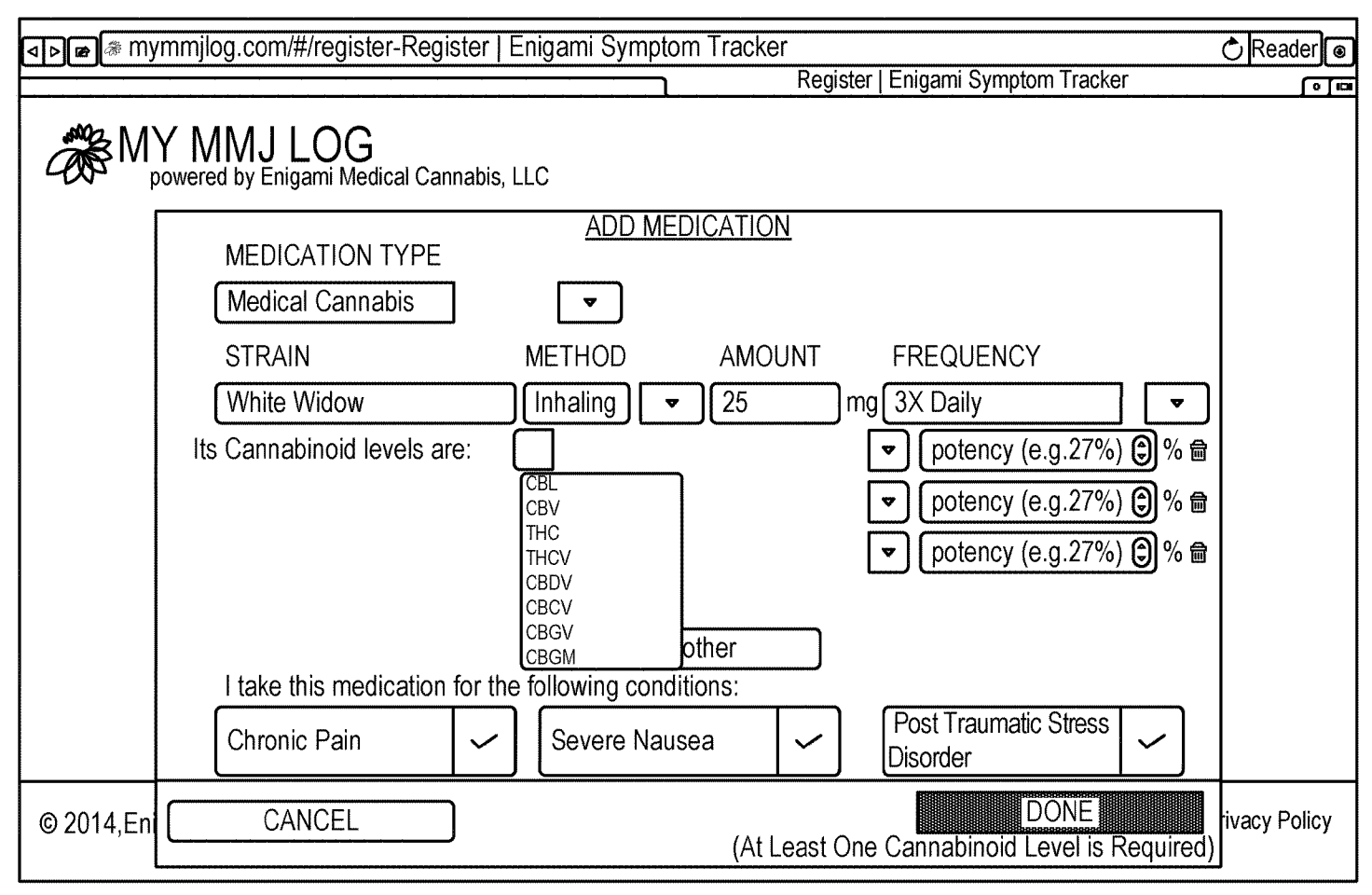

The system allows a user to drill down even further by providing information about the cannabinoids that are present in the cannabis product being monitored. In FIG. 17, a user can select from at least 15 cannabinoids, for example, to define the cannabinoid properties of a particular strain. Once a cannabinoid is selected from a drop down menu, the potency of that cannabinoid in that particular strain can be specified. Finally, a user can select the condition that the cannabinoid is being taken for. FIG. 18 shows additional cannabinoids in the cannabinoids drop down list.

Figure 19:
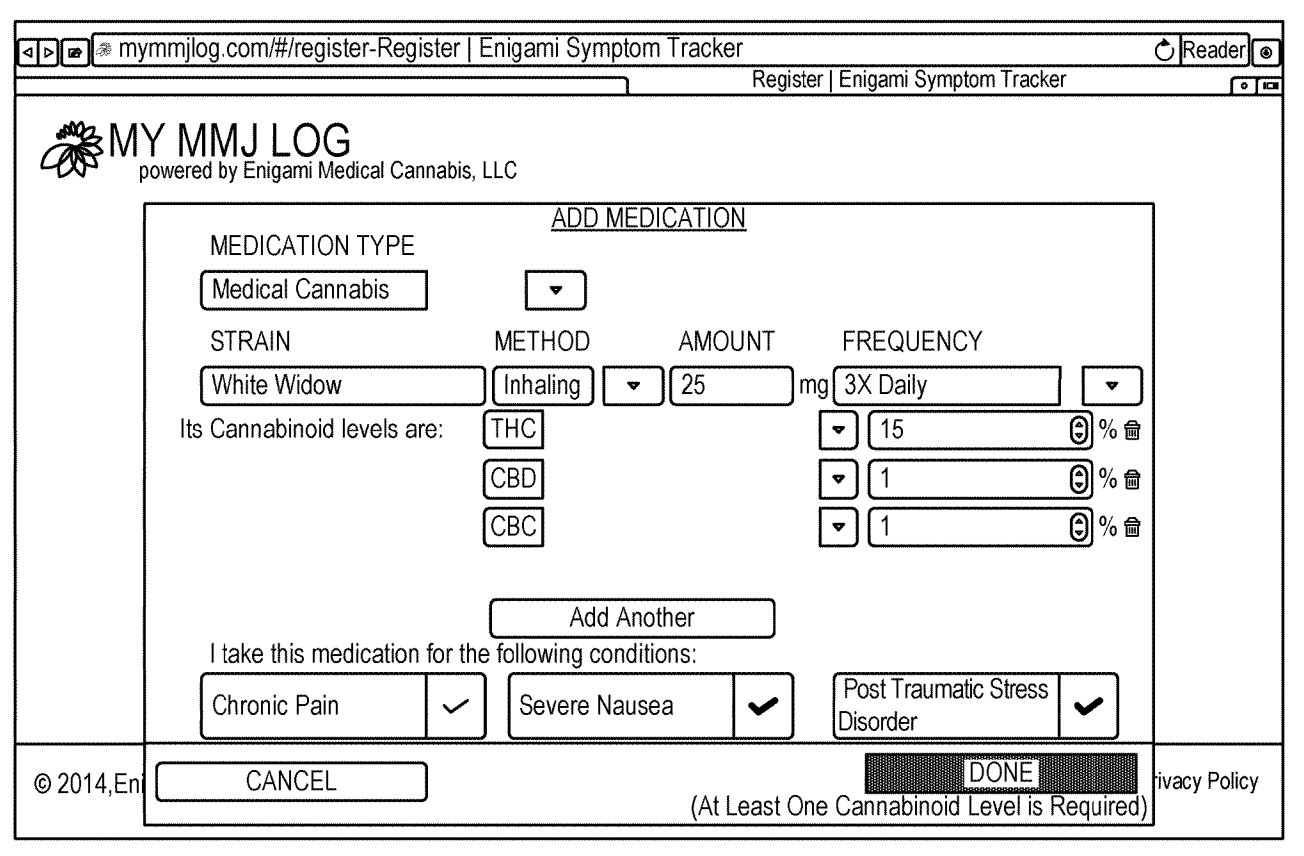

FIG. 19 illustrates an example once a medical cannabis medication has been fully specified. In FIG. 19, a user has selected the medication type as "Medical Cannabis." The strain has been identified as "White Widow." The method of administration has been identified as "Inhaling." The dosage amount has been specified as "25 mg." The frequency has been identified as "3× Daily." The cannabinoids in the White Widow product have been noted as 15% THC, 1% CBD, and 1% CBC. The conditions that the Medical Cannabis is being monitored for are "Severe Nausea" and "Post Traumatic Stress Disorder."

Figure 20:
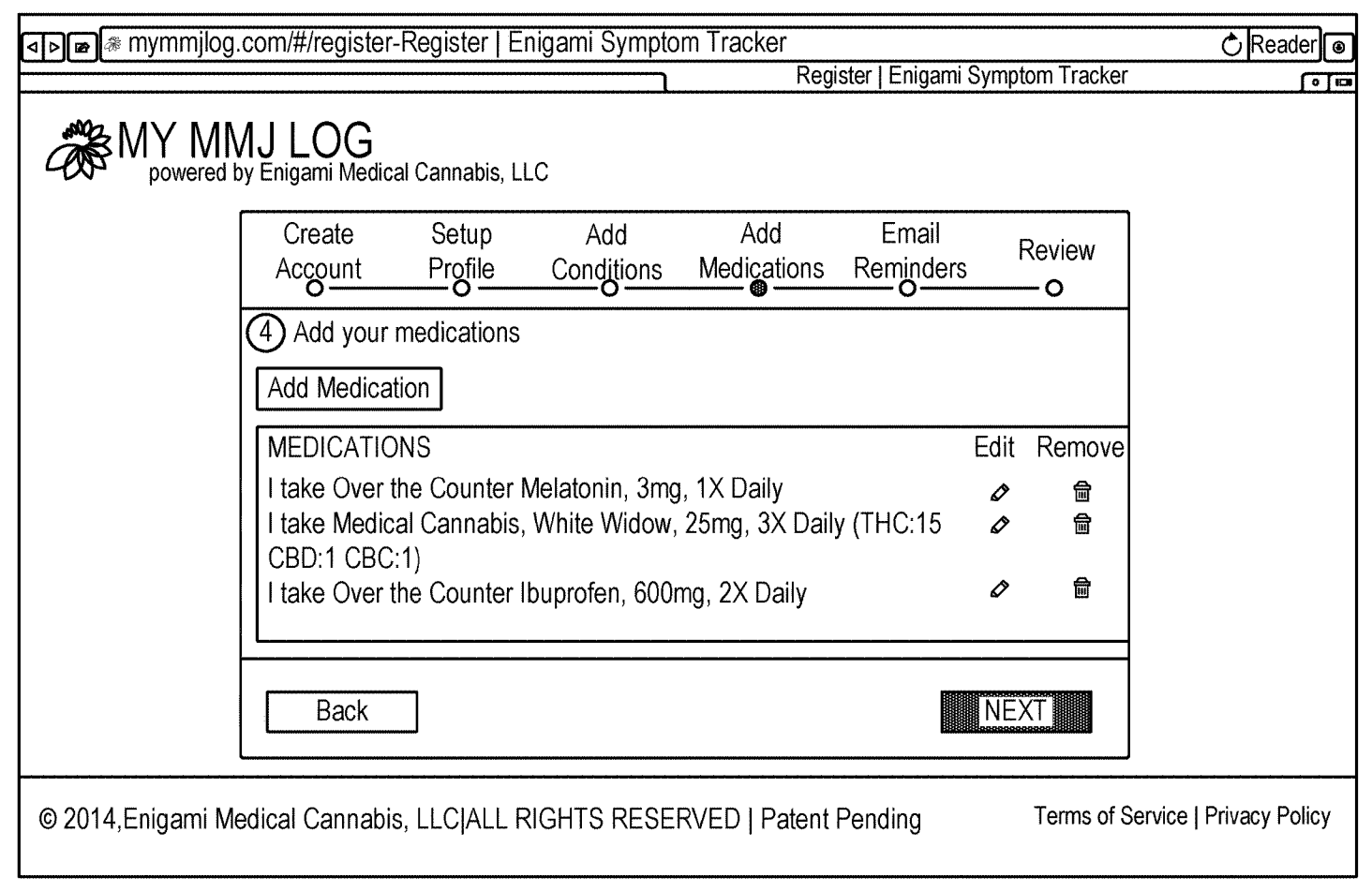

Once all the medications that a user wants to monitor have been entered, a user interface screen as shown in FIG. 20 can be displayed. This user interface screen allows a user to edit or remove different medications.

In accordance with one embodiment, a user can be sent email reminders about different conditions. This is shown, for example, in FIG. 21.

Figure 22:
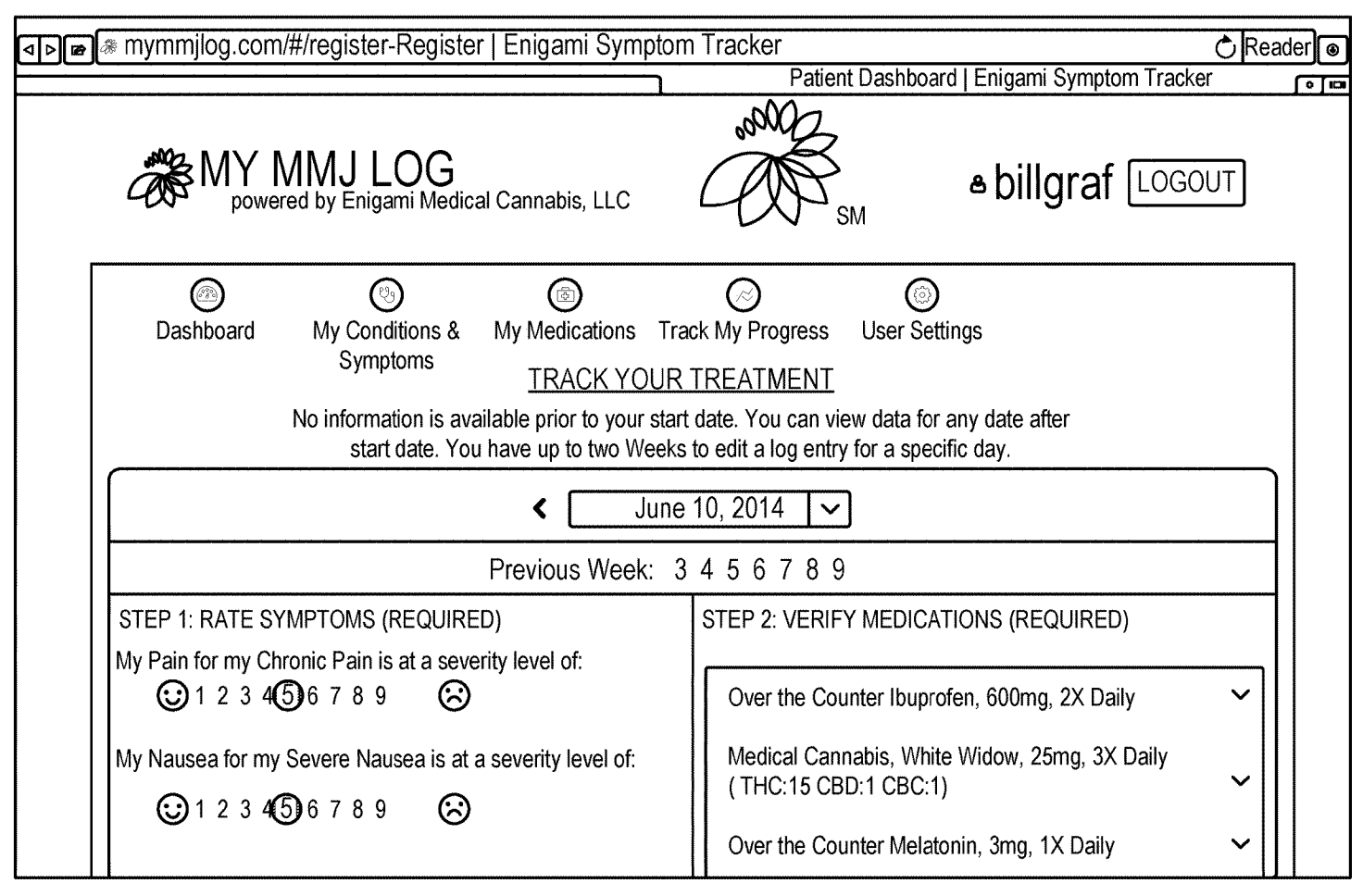

Once the condition(s)/symptom(s) and medications to be monitored have been entered into the monitoring system, the user can rate his/her symptoms on a periodic or intermittent basis. FIG. 22 illustrates that a user interface screen is displayed that allows a user to rate a symptom for a particular time period (e.g., how strong a symptom is for a particular day). In FIG. 22, a user selects a rating of his/her pain level on a scale of 1-9. Similarly, FIG. 22 shows that a user selects a rating of his/her nausea level on a scale of 1-9. FIG. 23 illustrates a second view of the user interface screen of FIG. 22 with the user interface scrolled down further. As can be seen, a user can also rate his/her difficulty falling or staying asleep. In addition, the user can select a rating of his/her feeling of detachment or estrangement from others. FIG. 23 also illustrates that a user can provide notes that might add useful information, such as changes to the user's regular routine, diet, or workout activity.

The system can also be used to provide immediate feedback to a user by displaying the progress to the user of the user's symptoms and medications. FIG. 24 illustrates an example of how the user's medications and symptoms can be graphed. By allowing the user to see the historical progress of the treatment, a user may be more likely to continue the process of entering information. This not only allows for positive reinforcement for the user, but also, greater lengths of time over which data may be collected.

Figure 25:
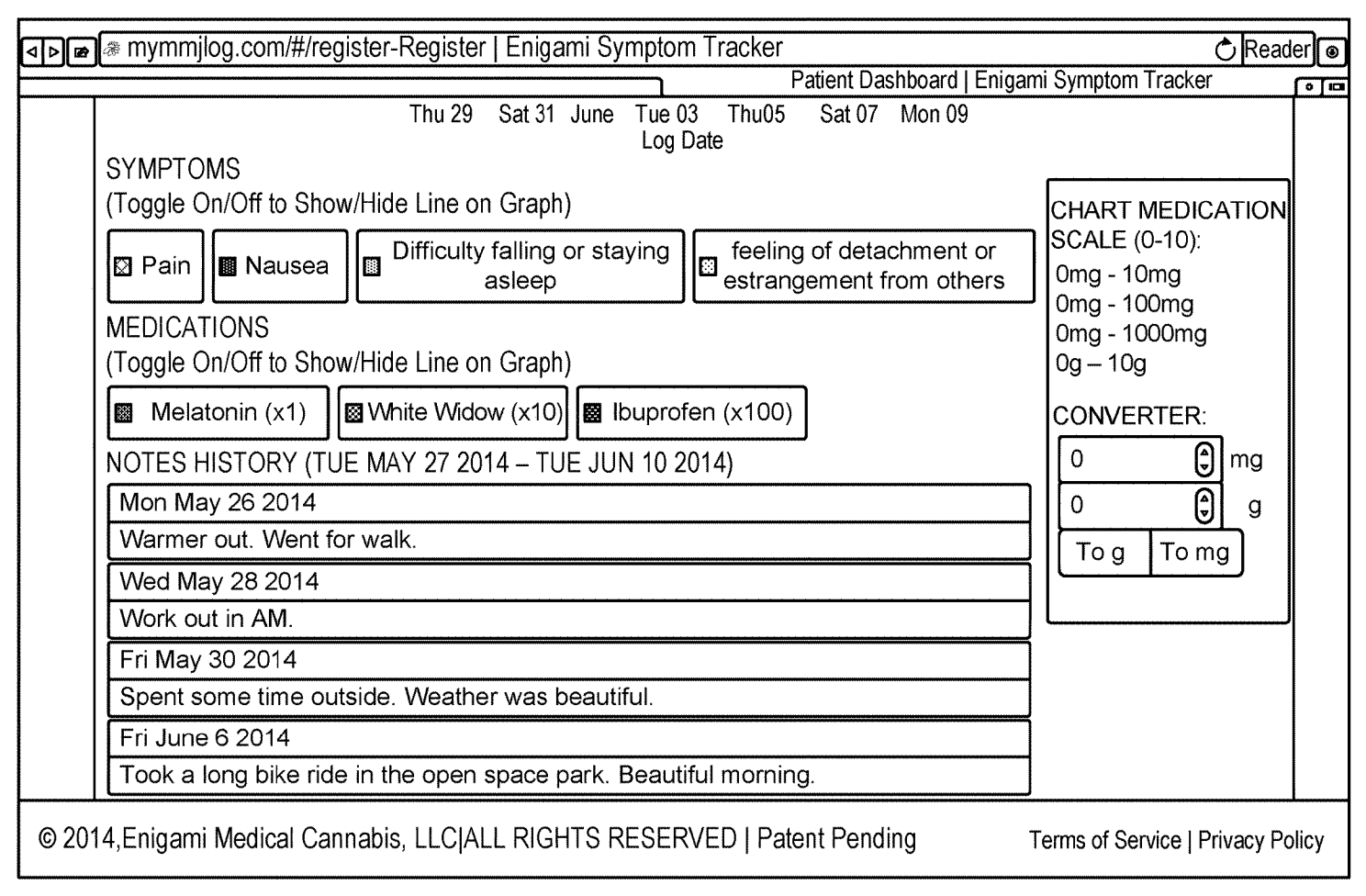
Figure 26:
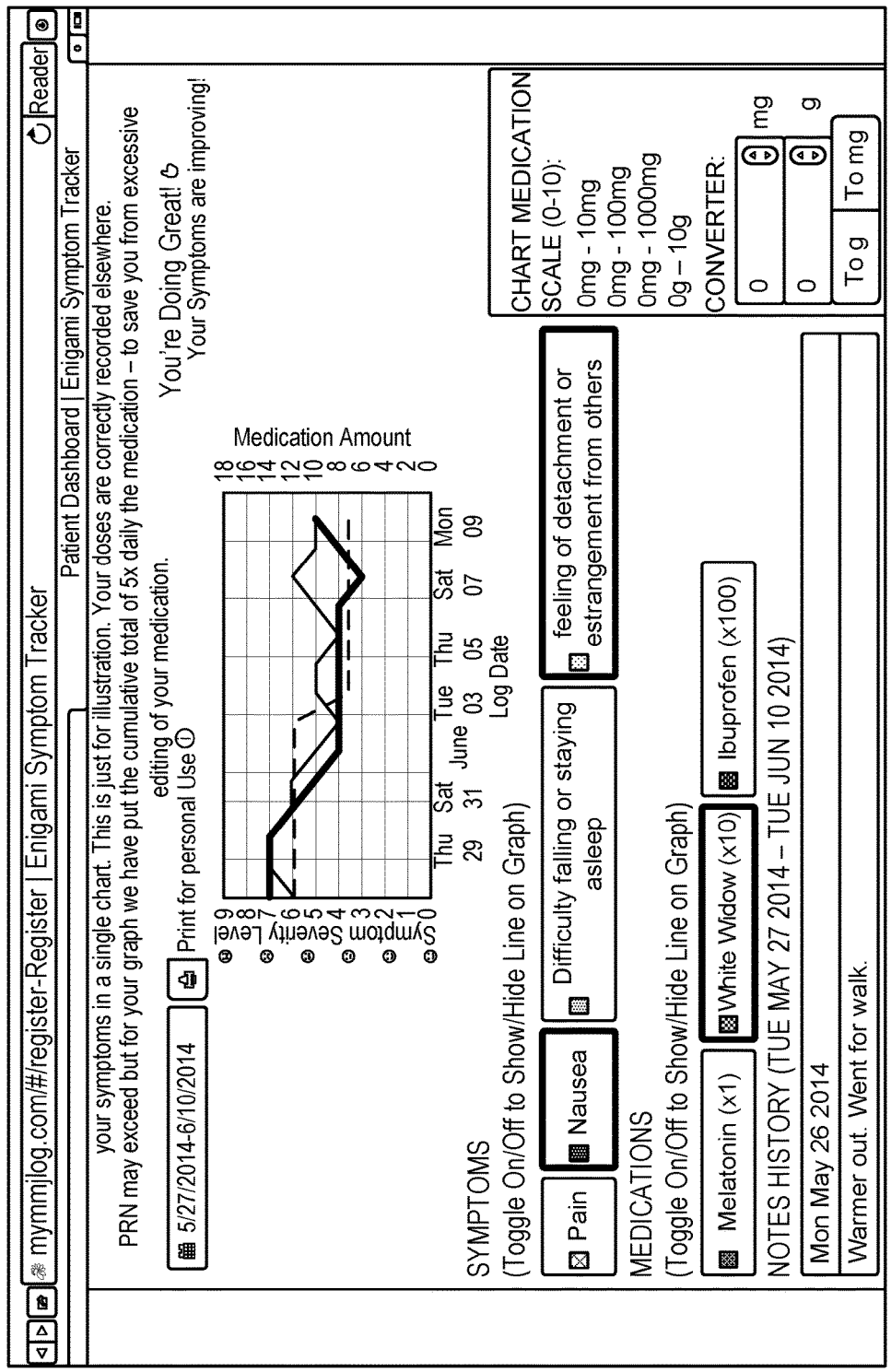
FIG. 26 illustrates another example of a user interface that displays selected symptom severity levels versus time/date as well as selected medication dosages versus time/date, in accordance with one embodiment.

FIG. 25 illustrates a further portion of the user interface screen shown in FIG. 24. In FIG. 25, one can see that the different symptoms are displayed and that the different medications are displayed. A color is shown as associated with each medication or symptom. This allows a user to easily identify the corresponding line on the graph of FIG. 24. A user can activate or deactivate the graph line for each medication and symptom. This allows a user to customize the graph in order to see how effective a particular medication is at relieving a particular symptom, for example. FIG. 26 illustrates an example of this in which the effect of the medical cannabis product defined as "White Widow" is graphed along with the symptom graphs for Nausea and Feeling of detachment or estrangement from others. As can be seen from the graph, the dashed line associated with the White Widow product initially is associated with a decrease in Nausea. And, after an initial increase in a Feeling of detachment, the user's Feeling of detachment decreased. When the dosage of the White Widow product was decreased, the Nausea symptom leveled off before later increasing and the user's feeling of detachment generally increased.

FIGS. 1 through 26 illustrate but one example of how a specially programmed computer can be implemented to monitor symptoms and medication. As noted above, this system can be very beneficial for the study of new drugs, medications, and substances. As one example, it can be used to study the effect of cannabis substances on condition(s)/symptom(s). It should be appreciated that the system need not be limited to the study of medical cannabis. The system may also be used to determine the relationship between recreational cannabis and symptoms. For example, the system could be utilized to determine which cannabinoid or combination of cannabinoids produced the most pleasing sensation of euphoria among users. Further, it should be appreciated that additional food, drinks, or supplements could be monitored by the system. For example, the use of mangos has been alleged to produce a longer lasting feeling of euphoria among recreational marijuana users. The system could accommodate the tracking of administration of such additional intakes of substances and whether the administration of such non-cannabinoid substances in combination with one or more cannabinoids produced a response.

Similarly, the system can be used to study what has been postulated as the "entourage effect." The entourage effect is postulated to be an effect or response produced by a combination of cannabinoids rather than a single cannabinoid. For example, while the cannabinoid THC is often attributed as producing a feeling of euphoria, some postulate that it is really a combination of THC with other specific cannabinoids that cause the feeling of euphoria. Thus, the system can be used to further research which combination of cannabinoids produce which entourage effects among participants.

The data entered by a user may be collected at a remote device and uploaded to a remote computer database. Alternatively, a site could be configured to allow a user to enter information into an account hosted remotely. An application service provider could be used that collects data entered by a user. In one embodiment a user could remotely enter information via a remote symptom monitoring service such as that disclosed in U.S. patent application Ser. No. 12/038,650 and 60/892,793 the contents of which are each hereby incorporated by reference in their entirety and for all purposes.

Figure 27:
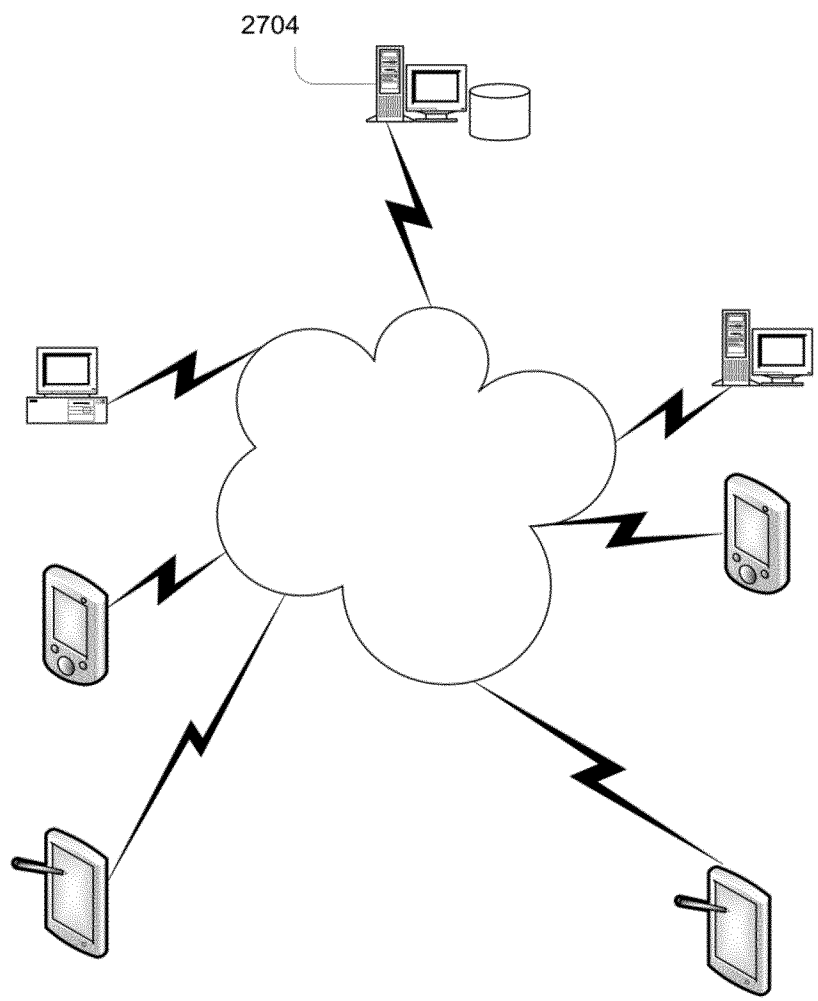
FIG. 27 illustrates an example of a system for collecting data, in accordance with one embodiment.

FIG. 27 illustrates an example of a system for collecting data. In FIG. 27 a computer server 2704 hosts a web site from which a program can be downloaded. Users who wish to monitor their medication can download the software to their individual computing devices. Each time a user enters information relating to symptom(s), condition(s), or medication(s), the information can be uploaded or stored by the server. FIG. 27 shows multiple users coupled with the server 2704 via a network, such as the internet.

Once the data from multiple users is acquired, the data can be processed to determine relationships between various medication(s)/substance(s) and/or combinations of medication(s)/substance(s) in the treatment of different symptom(s) and/or condition(s).

Figure 28:
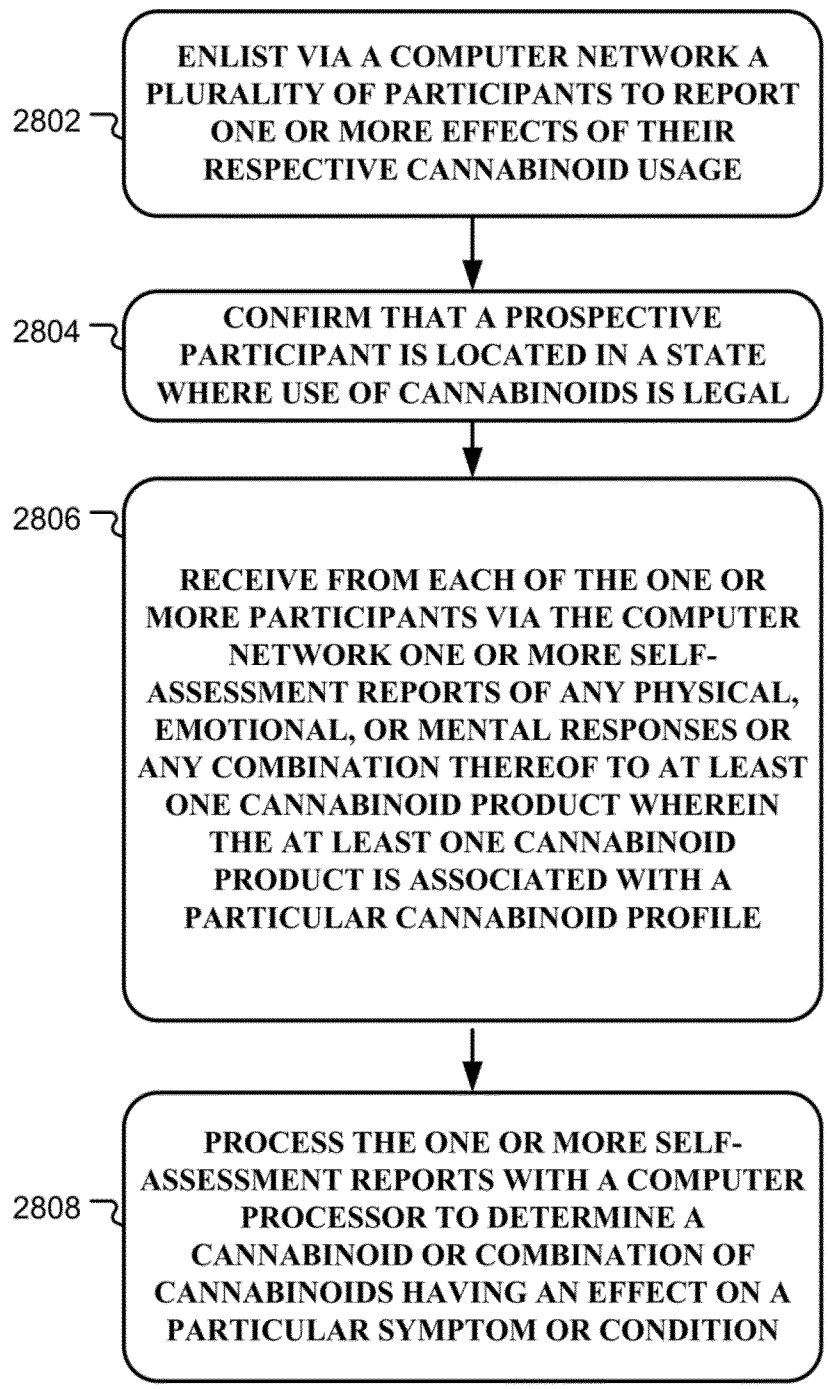
FIG. 28 is a flow chart that illustrates an example of determining how a substance can treat a particular symptom or condition, in accordance with one embodiment.

FIG. 28 shows a flow chart that helps to illustrate an example of gathering data from a large number of participants, for example with respect to cannabinoid usage. In operation block 2802, multiple participants are enlisted via a computer network to participate. The participants are enlisted to report the effect(s) that use of cannabinoid(s) has. The reported effects can relate to any symptom or condition that they suffer from as well as any physical, emotional, or mental response that they experience in response to the cannabinoid(s). Sometimes, a user will experience multiple responses, e.g., both a physical response and a mental response. All such responses can be reported in accordance with this example.

In operation block 2804, an entity that is coordinating user participation can confirm that a participant is located in a jurisdiction, e.g., a state or country, where use of cannabinoids is legally permitted. Such legal permission might only be at a state level and not at a federal level—however, a coordinating entity will likely want to ensure that some level of legality exists in the jurisdiction from which a prospective participant is participating. When a prospective participant enters his/her location, that location can be cross-referenced against a list of jurisdictions where cannabinoid usage is permitted.

A variety of ways can be used to check further on the prospective participant's location. For example, the prospective participant might be required to submit a copy of his or her driver's license and affirm under penalty of perjury that the cannabis will be consumed from a legal locale. Another option is that the internet protocol (IP) address of the prospective participant can be compared to the state which the prospective participant identifies as his/her present location. If the location associated with the IP address does not match the state that the prospective participant identifies, then the coordinating entity can perform additional verification step(s).

With the disclosed system, participants can participate from widely dispersed locations throughout a country as well as from different countries. Moreover, participants can also participate anonymously. This is beneficial when a substance that is being tested has a societal stigma attached to it, as in the case of marijuana.

Once a prospective participant is verified by the coordinating entity, the participant can begin submitting data via one or more self-assessment reports. The system described above with respect to FIGS. 1-27 can be used to allow a user to enter self-assessment data about their cannabinoid use and the effect that their cannabinoid use produces, e.g., physical, emotional, and/or mental responses and any effects on particular symptoms or conditions. This self-assessment data entered by the participant can then be conveyed via a computer network to the entity that will aggregate data from multiple participants. In some instances that entity will be the coordinating entity. In other instances, it might be a different entity.

As noted above, the number of cannabinoids and potency of those cannabinoids in different strains of cannabis can vary. Moreover, when cannabinoid products are manufactured, e.g., in the form of food or drinks, the number of cannabinoids and potency of those cannabinoids can vary across different manufacturing batches. Thus, the most accurate way to describe a cannabinoid substance is by its cannabinoid profile, i.e., by identifying the particular cannabinoids that a product contains and the potency of each of the identified cannabinoids.

In operation block 2808, the one or more self-assessment reports can be processed with a computer processor to determine a cannabinoid or combination of cannabinoids that have an effect on a particular symptom or condition. Moreover, the self-assessment reports can be processed to determine whether any prescription or non-prescription drugs that are taken along with a cannabinoid(s) produce an effect on a particular symptom or condition. For purposes of this patent, non-prescription drugs would include homeopathic, herbal, and other substances. Similarly, the self-assessment reports can be studied to determine if the use of cannabinoid(s) either alone or in combination with other substances produces any physical, mental, or emotional response(s). Such information might be useful for studying the effects of recreational marijuana, for example.

A variety of statistical analysis techniques could be used to find a statistical relationship between a cannabinoid and a response. Examples of statistical techniques are shown for example in "Choosing the Correct Statistical Test," available at bama.ua.edu/~jleeper/627/choosestat.html, last accessed on Jun. 12, 2015.

In addition to collecting data based on self-assessment reports of cannabinoids that a participant is currently taking, the system may also be used to inquire with a participant about other products that the participant might have taken in the past. Thus, if research shows that a particular cannabinoid profile is helpful in producing a particular response, participants can be polled or surveyed to see if they took a product having a similar cannabinoid profile in the past and whether it produced for them the particular response.

Figure 29:
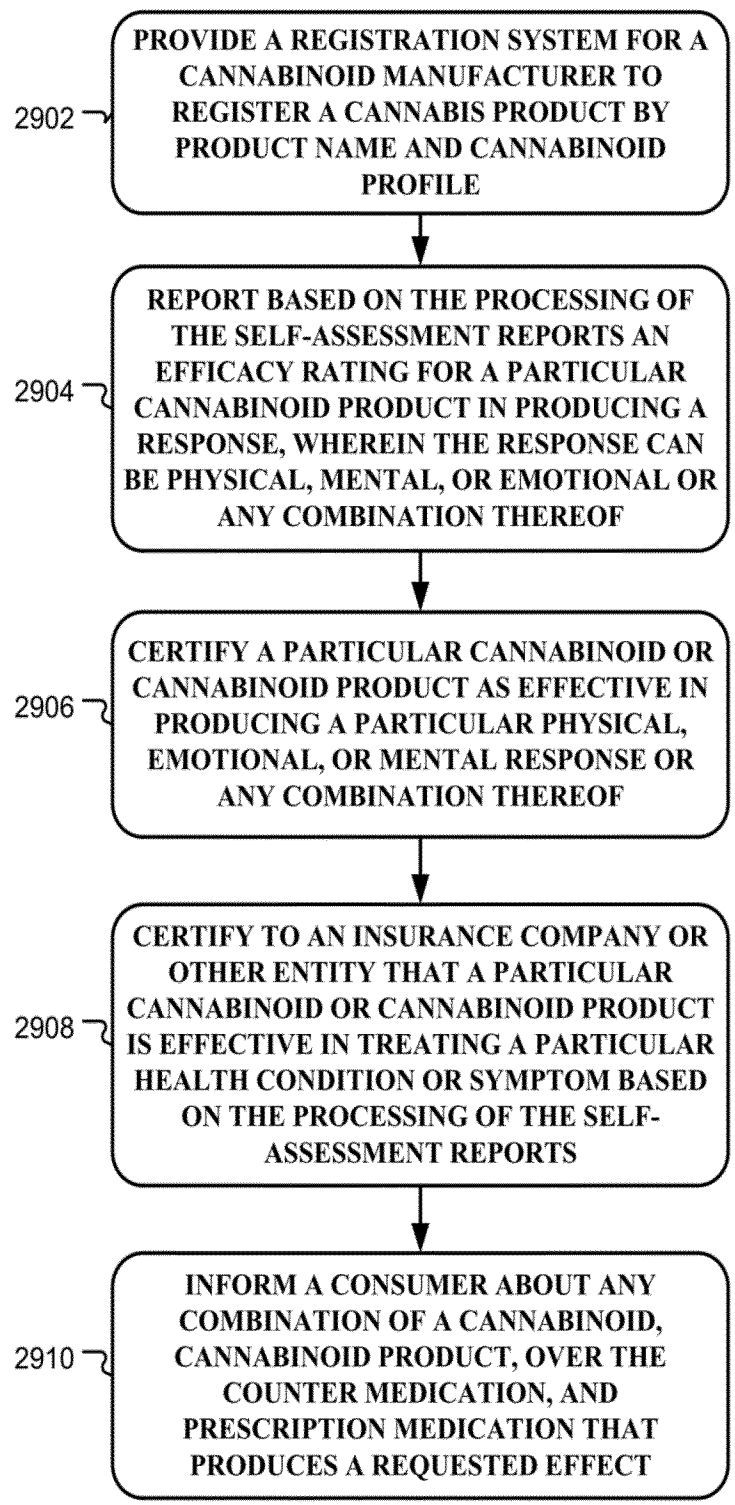
FIG. 29 is a flow chart that illustrates an example of certifying a substance for treating a particular symptom or condition, in accordance with one embodiment.

In accordance with one embodiment, the gathering of data about a particular substance can be put to use as part of a certification or recommendation system. This is illustrated, for example, in FIG. 29. In FIG. 29, a registration system is provided that allows a cannabinoid product manufacturer to submit information about a particular cannabis product, e.g., a product name and an associated cannabinoid profile for the product. In one embodiment, the product manufacturer could submit a sample of a product to be tested for a cannabinoid profile.

In operation 2904, a report can be generated that details the efficacy rating for a particular cannabinoid product in producing a response. As noted herein, the response might be a physical, mental, or emotional response, or any combination thereof. The efficacy rating and report can be generated based on self-assessment reports submitted by study participants.

Moreover, the efficacy rating for a particular cannabinoid product can be certified to a third party. Operation block 2906 illustrates that a particular cannabinoid product is first verified as producing a particular physical, emotional, or mental response or any combination thereof. And, operation block 2908 illustrates that such verified results can be reported to an inquiring third party such as an insurance company, a caregiver, a healthcare organization, a commercial vendor, a government agency, such as the Food and Drug Agency or other government agency or program, such as Medicare, Medicaid, Veterans Health System, Veterans Health Administration, or some other third party. Thus, an entity that is interested in using a substance like marijuana for its patients can rely upon a reliable authority as to what response the patient is likely to have to the marijuana.

The system can also recommend to a consumer a cannabinoid, a combination of cannabinoids, or at least one cannabinoid in combination with a non-cannabinoid that will produce a desired response. This can be useful to a person who is thinking of using a cannabinoid product for the first time and wants to know which particular product or cannabinoid profile will generate a desired response.

In operation block 2910, a consumer can be informed of a combination of cannabinoids, or at least one cannabinoid in combination with a non-cannabinoid that will produce a desired response.

Figure 30:
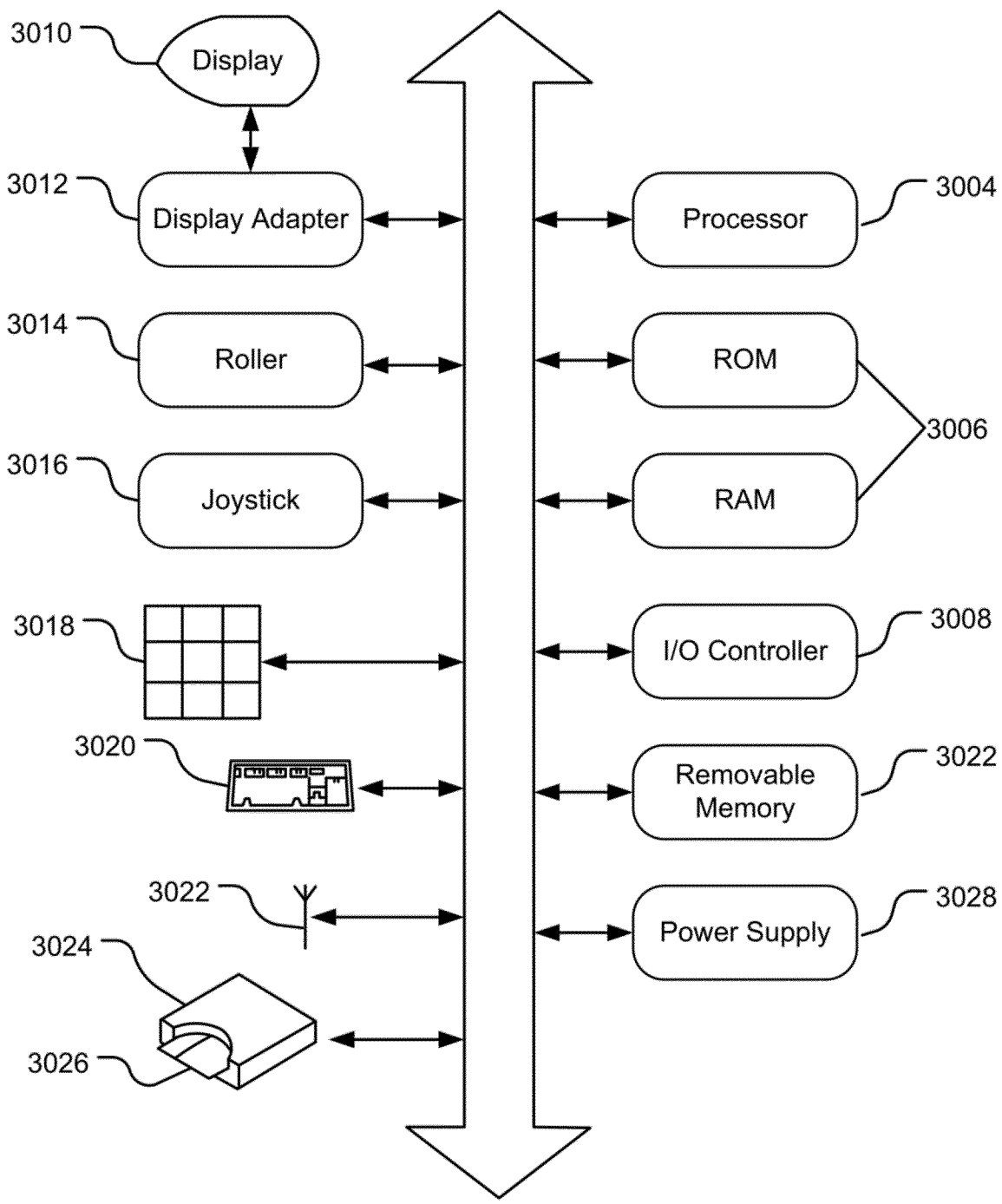
FIG. 30 illustrates a block diagram of a computer system in accordance with one embodiment.

FIG. 30 discloses a block diagram of a computer system 3000 suitable for implementing aspects of at least one implementation. As shown in FIG. 30, system 3000 includes a bus 3002 which interconnects major subsystems such as a processor 3004, internal memory 3006 (such as a RAM or ROM), an input/output (I/O) controller 3008, removable memory (such as a memory card) 3022, an external device such as a display screen 3010 via a display adapter 3012, a roller-type input device 3014, a joystick 3016, a numeric keyboard 3018, an alphanumeric keyboard 3020, smart card acceptance device 3024, a wireless interface 3026, and a power supply 3028. Many other devices can be connected. Wireless interface 3026 together with a wired network interface (not shown), may be used to interface to a local or wide area network (such as the Internet) using any network interface system known to those skilled in the art.

Many other devices or subsystems (not shown) may be connected in a similar manner. For example, a module that facilitates voice-activated commands may be implemented. Also, it is not necessary for all of the devices shown in FIG. 30 to be present to practice an embodiment. Furthermore, the devices and subsystems may be interconnected in different ways from that shown in FIG. 30. Code to implement one embodiment may be operably disposed in the internal memory 3006 or stored on storage media such as the removable memory 3022, a floppy disk, a thumb drive, a CompactFlash® storage device, a DVD-R ("Digital Versatile Disc" or "Digital Video Disc" recordable), a DVD-ROM ("Digital Versatile Disc" or "Digital Video Disc" read-only memory), a CD-R (Compact Disc-Recordable), or a CD-ROM (Compact Disc read-only memory). For example, in an embodiment of the computer system 3000, code for implementing the supplemental keyword generation tool may be stored in the internal memory 3006 and configured to be operated by the processor 3004.

In the above description, for the purposes of explanation, numerous specific details are set forth in order to provide a thorough understanding of the embodiments described. It will be apparent, however, to one skilled in the art that these embodiments may be practiced without some of these specific details. For example, while various features are ascribed to particular embodiments, it should be appreciated that the features described with respect to one embodiment may be incorporated with other embodiments as well. By the same token, however, no single feature or features of any described embodiment should be considered essential, as other embodiments may omit such features.

In the interest of clarity, not all of the routine functions of the embodiments described herein are shown and described. It will, of course, be appreciated that in the development of any such actual embodiment, numerous implementation-specific decisions must be made in order to achieve the developer's specific goals, such as compliance with application—and business-related constraints, and that those specific goals will vary from one embodiment to another and from one developer to another.

According to one embodiment, the components, process steps, and/or data structures disclosed herein may be implemented using various types of operating systems (OS), computing platforms, firmware, computer programs, computer languages, and/or general-purpose machines. The method can be run as a programmed process running on processing circuitry. The processing circuitry can take the form of numerous combinations of processors and operating systems, connections and networks, data stores, or a standalone device. The process can be implemented as instructions executed by such hardware, hardware alone, or any combination thereof. The software may be stored on a program storage device readable by a machine.

According to one embodiment, the components, processes and/or data structures may be implemented using machine language, assembler, PHP, C or C++, Java and/or other high level language programs running on a data processing computer such as a personal computer, workstation computer, mainframe computer, or high performance server running an OS such as Solaris® available from Sun Microsystems, Inc. of Santa Clara, Calif., Windows 8, Windows 7, Windows Vista™, Windows NT®, Windows XP PRO, and Windows® 2000, available from Microsoft Corporation of Redmond, Wash., Apple OS X-based systems, available from Apple Inc. of Cupertino, Calif., or various versions of the Unix operating system such as Linux available from a number of vendors. The method may also be implemented on a multiple-processor system, or in a computing environment including various peripherals such as input devices, output devices, displays, pointing devices, memories, storage devices, media interfaces for transferring data to and from the processor(s), and the like. In addition, such a computer system or computing environment may be networked locally, or over the Internet or other networks. Different implementations may be used and may include other types of operating systems, computing platforms, computer programs, firmware, computer languages and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used without departing from the scope and spirit of the inventive concepts disclosed herein.

The above specification, examples, and data provide a complete description of the structure and use of exemplary embodiments of the invention. Furthermore, structural features of the different implementations may be combined in yet another implementation without departing from the recited claims.

What is claimed is:

1. A method comprising:
enlisting via a computer network a plurality of participants to report one or more experienced effects from their respective cannabinoid usage;
confirming that a prospective participant is located in a jurisdiction where use of cannabinoids is legal;
receiving from each of the one or more participants via the computer network one or more self-assessment reports of one or more physical, emotional, or mental reported effects or one or more combination thereof from the use of at least one administered cannabinoid product wherein the at least one administered cannabinoid product is associated with a particular cannabinoid profile;
processing the one or more self-assessment reports with a computer processor to determine a cannabinoid or combination of cannabinoids having an effect on a particular symptom or medical condition; and
recommending an administration of a particular product to a consumer to treat the particular symptom or medical condition.

2. The method of claim 1 wherein the processing the one or more self-assessment reports comprises:
statistically evaluating the one or more self-assessment reports with the computer processor to determine the cannabinoid or the combination of cannabinoids having the determined effect on the particular symptom or the particular medical condition.

3. The method of claim 1 wherein not all of the plurality of participants participate from the same country.

4. The method of claim 1 and wherein at least a portion of the participants participate anonymously.

5. The method of claim 1 and further comprising:
reporting an efficacy rating for a particular cannabinoid product in producing a designated-effect, wherein the designated effect can be physical, mental, or emotional or any combination thereof.

6. The method of claim 1 and further comprising:
certifying a particular cannabinoid or cannabinoid product as effective in treating a particular health condition or symptom.

7. The method of claim 1 and further comprising:
certifying a particular cannabinoid or cannabinoid product as effective in producing a particular physical, emotional, or mental certified effect or any combination thereof.

8. The method of claim 1 and further comprising:
providing a registration system for a cannabinoid manufacturer to register a cannabis product by product name and cannabinoid profile.

9. The method of claim 1 wherein a participant can enter information about a cannabis product by product name and cannabinoid profile.

10. The method of claim 1 and further comprising:
statistically analyzing the self-assessment reports with the computer processor to determine a combination of cannabinoids having an entourage effect.

11. The method of claim 1 and further comprising:
statistically analyzing the self-assessment reports with the computer processor to determine a combination of one or more cannabinoids having a synergistic effect with an over the counter medication, a prescription medication, or a combination thereof.

12. The method of claim 1 and further comprising:
certifying to an insurance company that a particular cannabinoid or cannabinoid product is effective in treating a particular health condition or symptom based on a statistical analysis of the self-assessment reports.

13. The method of claim 1 and further comprising:
certifying to a caregiver that a particular cannabinoid or cannabinoid product is effective in treating a particular health condition or symptom based on a statistical analysis of the self-assessment reports.

14. The method of claim 1 and further comprising:
certifying to a healthcare organization that a particular cannabinoid or cannabinoid product is effective in treating a particular health condition or symptom based on a statistical analysis of the self-assessment reports.

15. The method of claim 1 and further comprising:
certifying to a governmental entity that a particular cannabinoid or cannabinoid product is effective in treating a particular health condition or symptom based on a statistical analysis of the self-assessment reports.

16. The method of claim 1 and further comprising:
certifying to a commercial vendor that a particular cannabinoid or cannabinoid product is effective in treating a particular health condition or symptom based on a statistical analysis of the self-assessment reports.

17. The method of claim 1 wherein the recommending comprises:
recommending to the consumer a cannabinoid, combination of cannabinoids, or cannabinoid product.

18. The method of claim 1 wherein the recommending comprises:
recommending to the consumer one or more combinations of a cannabinoid, cannabinoid product, over the counter medication, or prescription medication.

19. The method of claim 17 and further comprising:
determining a physical, emotional, or mental desired effect or any combination thereof desired by a consumer prior to the recommending.

20. The method of claim 1 and further comprising:
inquiring with a participant about a cannabis product that the participant is not currently taking but has previously taken.

21. The method of claim 1 wherein confirming that the prospective participant is located in a jurisdiction where use of cannabinoids is legal comprises checking the internet protocol address of the prospective participant.

22. The method of claim 2 wherein the particular medical condition comprises a plurality of symptoms.

23. The method of claim 2 and further comprising:
reporting based on the statistical evaluation of the self-assessment reports an efficacy rating for a particular cannabinoid product in producing a designated effect, wherein the designated effect can be physical, mental, or emotional or any combination thereof.

24. The method of claim 22 and further comprising:
certifying a particular cannabinoid or cannabinoid product as effective in treating the particular medical condition or the particular symptom based on the statistical evaluation of the self-assessment reports.

* * * * *

UNITED STATES PATENT AND TRADEMARK OFFICE
CERTIFICATE OF CORRECTION

PATENT NO. : 10,319,475 B1
APPLICATION NO. : 14/739723
DATED : June 11, 2019
INVENTOR(S) : Croan et al.

Page 1 of 5

It is certified that error appears in the above-identified patent and that said Letters Patent is hereby corrected as shown below:

On the Title Page

Under abstract "24 Claims, 26 Drawing Sheets" should read --24 Claims, 30 Drawing Sheets--.

In the Drawings

Please add FIGS. 27, 28, 29 and 30 as shown on the attached pages.

Signed and Sealed this
Fourteenth Day of January, 2020

Andrei Iancu
*Director of the United States Patent and Trademark Office*